(12) United States Patent
Ozyilmaz et al.

(10) Patent No.: US 11,114,674 B2
(45) Date of Patent: Sep. 7, 2021

(54) PROTON CONDUCTIVE TWO-DIMENSIONAL AMORPHOUS CARBON FILM FOR GAS MEMBRANE AND FUEL CELL APPLICATIONS

(71) Applicant: NATIONAL UNIVERSITY OF SINGAPORE, Singapore (SG)

(72) Inventors: Barbaros Ozyilmaz, Singapore (SG); Henrik Andersen, Singapore (SG); Chee Tat Toh, Singapore (SG)

(73) Assignee: National University of Singapore, Singapore (SG)

( * ) Notice: Subject to any disclaimer, the term of this patent is extended or adjusted under 35 U.S.C. 154(b) by 107 days.

(21) Appl. No.: 16/049,034

(22) Filed: Jul. 30, 2018

(65) Prior Publication Data

US 2018/0337411 A1 Nov. 22, 2018

Related U.S. Application Data

(63) Continuation-in-part of application No. 15/901,099, filed on Feb. 21, 2018.
(Continued)

(30) Foreign Application Priority Data

Feb. 23, 2018 (WO) ................ PCT/SG2018/050082

(51) Int. Cl.
*H01M 4/98* (2006.01)
*H01M 4/88* (2006.01)
(Continued)

(52) U.S. Cl.
CPC .......... *H01M 4/98* (2013.01); *C23C 14/0005* (2013.01); *C23C 16/01* (2013.01); *C23C 16/27* (2013.01); *H01M 4/8657* (2013.01); *H01M 4/8803* (2013.01); *H01M 8/1023* (2013.01); *H01M 8/1039* (2013.01); *H01M 8/1053* (2013.01); *H01M 2008/1095* (2013.01)

(58) Field of Classification Search
None
See application file for complete search history.

(56) References Cited

U.S. PATENT DOCUMENTS 4,725,345 A 2/1988 Sakamoto et al.
5,266,409 A 11/1993 Schmidt et al.
(Continued)

FOREIGN PATENT DOCUMENTS

DE 102009034573 A1 * 2/2010 .......... H01M 8/0206
DE 102009034573 A1 2/2010
(Continued)

OTHER PUBLICATIONS

Meyer et al.; Toward Two-Dimensional All-Carbon Heterostructures via Ion Beam Petterning of Single-Laeyer Graphene; Nano Lett.; 5944-5949; 2015.*
(Continued)

*Primary Examiner* — Guinever S Gregorio
(74) *Attorney, Agent, or Firm* — Ajay A. Jagtiani; Miles & Stockbridge P.C

(57) ABSTRACT

Described is a fuel cell comprising an electrode catalyst assembly, and a two-dimensional (2D) amorphous carbon, wherein the 2D amorphous carbon has a crystallinity (C)≤0.8.

19 Claims, 16 Drawing Sheets

Related U.S. Application Data

(60) Provisional application No. 62/549,680, filed on Aug. 17, 2017, provisional application No. 62/463,112, filed on Feb. 24, 2017.

(51) Int. Cl.
| | |
|---|---|
| H01M 4/86 | (2006.01) |
| C23C 14/00 | (2006.01) |
| C23C 16/01 | (2006.01) |
| C23C 16/27 | (2006.01) |
| H01M 8/1023 | (2016.01) |
| H01M 8/1053 | (2016.01) |
| H01M 8/1039 | (2016.01) |
| H01M 8/1018 | (2016.01) |

(56) References Cited

U.S. PATENT DOCUMENTS

| | | | |
|---|---|---|---|
| 5,397,644 | A | 3/1995 | Yamashita |
| 5,989,672 | A | 11/1999 | Hayashi |
| 8,941,950 | B2 | 1/2015 | Yuan et al. |
| 2002/0051903 | A1* | 5/2002 | Masuko .............. H01M 4/8605 423/449.1 |
| 2011/0048943 | A1* | 3/2011 | Nemes ................ G01N 27/4045 204/415 |
| 2011/0129675 | A1 | 6/2011 | Choi et al. |
| 2011/0151278 | A1 | 6/2011 | Gurney et al. |
| 2011/0290655 | A1 | 12/2011 | Nishikiori et al. |
| 2013/0214875 | A1 | 8/2013 | Duncan et al. |
| 2014/0248513 | A1 | 9/2014 | Takizawa et al. |
| 2015/0093684 | A1 | 4/2015 | Yadav et al. |
| 2016/0036801 | A1 | 2/2016 | Moghaddam et al. |
| 2016/0111180 | A1 | 4/2016 | Joo et al. |
| 2017/0032815 | A1 | 2/2017 | Oezyilmaz et al. |
| 2017/0186457 | A1 | 6/2017 | Ng et al. |
| 2017/0263966 | A1 | 9/2017 | Lozada et al. |
| 2019/0080713 | A1 | 3/2019 | Oezyilmaz et al. |
| 2019/0088420 | A1 | 3/2019 | Tour et al. |

FOREIGN PATENT DOCUMENTS

| | | |
|---|---|---|
| JP | 09091686 A | 9/1995 |
| JP | 2002143185 A | 5/2002 |
| JP | 02002312923 A | 10/2002 |
| WO | 03/065881 A2 | 8/2003 |

OTHER PUBLICATIONS

Kim et al.; Mass Transport through a Proton Exchange Membrane Nation in Microbial Fuel Cells; Energy & Fuels; 22, 169-176; 2008.*

Ferrari, A.C. et al. "Interpretation of Raman spectra of disordered and amorphous carbon." Physical Review B 61, 14095-14107 (2000).

Robertson, J. "Ultrathin carbon coatings for magnetic storage technology." Thin Solid Films 383, 81-88 (2001).

Hu, S. et al. "Proton transport through one-atom-thick crystals." Nature 516, 227-230 (2014).

Das, S. et al. "Measurements of adhesion energy of graphene to metallic substrates." Carbon 59, 121-129 (2013).

Schriver, M. et al. "Graphene as a Long-Term Metal Oxidation Barrier: Worse Than Nothing" ACS Nano 7, 5763-5768 (2013).

Wang, J. S. et al. "The mechanical performance of DLC films on steel substrates." Thin Solid Films 325, 163-174 (1998).

Leng, Y. X. et al. "Mechanical properties and platelet adhesion behavior of diamond-like carbon films synthesized by pulsed vacuum arc plasma deposition." Surface Science 531, 177-184 (2003).

Maguire, P. D. et al. "Mechanical stability, corrosion performance and bioresponse of amorphous diamond-like carbon for medical stents and guidewires." Diamond and Related Materials 14, 1277-1288 (2005).

Marcon, et. al. "The head-disk interface roadmap to an areal density of 4 Tbit/in2." Advances in Tribology 2013, 1-8 (2013).

Discher, D. E., Mooney, D. J. & Zandstra, P. W. "Growth Factors, Matrices, and Forces Combine and Control Stem Cells." Science 324, 1673-1677 (2009).

Spradling, A., Drummond-Barbosa, D. & Kai, T. "Stem cells find their niche." Nature 414, 98-104 (2001).

Murry, C. E. & Keller, G. "Differentiation of Embryonic Stem Cells to Clinically Relevant Populations: Lessons from Embryonic Development." Cell 132, 661-680 (2008).

Engler, A. J., Sen, S., Sweeney, H. L. & Discher, D. E. "Matrix Elasticity Directs Stem Cell Lineage Specification." Cell 126, 677-689 (2006).

Dalby, M. J. et al. "The control of human mesenchymal cell differentiation using nanoscale symmetry and disorder." Nature Materials 6, 997-1003 (2007).

Trappmann, B. et al. "Extracellular-matrix tethering regulates stem-cell fate." Nature Materials 11, 642-649 (2012).

Lee, H. et al. "Establishment of feeder-free culture system for human induced pluripotent stem cell on DAS nanocrystalline graphene." Scientific Reports 6, 20708 (2016).

Choi, W. J. et al. "Effects of substrate conductivity on cell morphogenesis and proliferation using tailored, atomic layer deposition-grown ZnO thin films." Scientific Reports 5, 9974 (2015).

Sharaf, O. Z. & Orhan, M. F. "An overview of fuel cell technology: Fundamentals and applications." Renewable and Sustainable Energy Reviews 32, 810-853 (2014).

Schmittinger, W. & Vahidi, A. "A review of the main parameters influencing long-term performance and durability of PEM fuel cells." Journal of Power Sources 180, 1-14 (2008).

Reiser, C. A. "A reverse-current decay mechanism for fuel cells." J Electrochem Solid-State Letters 8, A273-A276 (2005).

Li, X. S. et al. Large-Area Synthesis of High-Quality and Uniform Graphene Films on Copper Foils Science 324, 1312-1314 (2009).

Lozada-Hidalgo et al., "Sieving hydrogen isotopes through two-dimensional crystals", Science, vol. 351, Issue 6268, pp. 68-70 (2016).

Office Action received in U.S. Appl. No. 15/901,099 dated Apr. 1, 2020.

Office Action received in U.S. Appl. No. 16/049,034 dated Mar. 31, 2020.

Kotakoski et al., "Toward Two-Dimensional All-Caron Heterostructures via Ion Beam Patterning of Single-Layer Graphene", Nano Letters, vol. 15, pp. 5944-5949 (2015).

Zhao et al., "Sythesis of large-scale undoped and nitrogen-doped amorphous graphene on MgO substrate by chemical vapor deposition", Journal of Materials Chemistry, vol. 22, pp. 19679-19683 (2012).

Chae et al., "Mass Transport through a Proton Exchange Membrane (Nafion) in Microbial Fuel Cells", Energy & Fuels, 22, pp. 169-176 (2008).

Office Action received in U.S. Appl. No. 15/901,099 dated Aug. 19, 2020.

Office Action received in U.S. Appl. No. 16/049,034 dated Aug. 21, 2020.

Office Action received in U.S. Appl. No. 16/181,656 dated Aug. 19, 2020.

Office Action received in U.S. Appl. No. 16/181,656 dated Dec. 3, 2020.

Extended European Search Report received in European Application No. 18757600.4 dated Nov. 19, 2020.

International Preliminary Report on Patentability received in International Application No. PCT/SG2018/050082 dated Aug. 27, 2019.

International Search Report received in International Application No. PCT/SG2018/050082 dated May 14, 2018.

Casiraghi et al., "Dynamic Roughening of Tetrahedral Amorphous Carbon", Physical Review Letters, vol. 91, No. 22, pp. 226104-1-226104-4 (2003).

D'Angelo et al., "Micropatterned Hydrogenated Amorphous Carbon Guides Mesenchymal Stem Cells Towards Neuronal Differentiation", European Cells and Materials, vol. 20, pp. 231-244 (2010).

(56) References Cited

OTHER PUBLICATIONS

Mattioli et al., "Nanostructured Polystyrene Films Engineered by Plasma Processes: Surface Characterization and Stem Cell Interaction", Journal of Applied Polymer Science, pp. 40427 (1-10) (2014).
Joo et al., "Realization of continuous Zachariasen carbon monolayer", Science Advances, vol. 3, pp. 1-8 (2017).
Kotakoski et al., "From Point Defects in Graphene to Two-Dimensional Amorphous Carbon", Physical Review Letters, vol. 106, No. 10, pp. 105505-1-105505-4 (2011).
Suk et al., Mechanical measurements of ultra-thin amorphous carbon membranes using scanning atomic force microscopy, Carbon, vol. 50, No. 6, pp. 2220-2225 (2012).
Office Action received in Japanese Application No. 2019-546155 dated Nov. 17, 2020.
Dwivedi et al., "Understanding the Role of Nitrogen in Plasma-Assisted Surface Modification of Magnetic Recording Media with and without Ultrathin Carbon Overcoats", Scientific Reports, vol. 5; No. 7772; pp. 1-13 (2015).
Pathem et al., Carbon Overcoat Oxidation in Heat-Assisted Magnetic Recording; IEEE Transactions on Magentics; vol. 49; No. 7; pp. 3721-3724 (2013).
International Search Report and Written Opinion received in International Application No. PCT/SG2019/050374 dated Oct. 3, 2019.
Office Action received in U.S. Appl. No. 15/901,099 dated Jan. 13, 2021.

\* cited by examiner

500

PROTON CONDUCTIVE TWO-DIMENSIONAL AMORPHOUS CARBON FILM FOR GAS MEMBRANE AND FUEL CELL APPLICATIONS

CROSS-REFERENCE TO RELATED APPLICATIONS

This application claims benefit of priority of U.S. patent application Ser. No. 15/901,099 entitled, "Two-Dimensional Amorphous Carbon Coating and Methods of Growing and Differentiating Stem Cells," filed Feb. 21, 2018, PCT International Application No. PCT/SG2018/050082 filed Feb. 23, 2018, which claims priority to U.S. Provisional Patent Application No. 62/546,680 entitled, "Therapeutic Coating and Methods of Growing and Differentiating Stem Cells," filed Aug. 17, 2017 and U.S. Provisional Application No. 62/463,112 entitled, "Layered Composite Material Consisting Atomically Thin Amorphous Carbon on Top of the Substrate," filed Feb. 24, 2017. The entire contents and disclosures of these patent applications are incorporated herein by reference in their entirety.

BACKGROUND

Field of the Invention

The present disclosure relates to generally to two-dimensional amorphous carbon (2DAC) coating techniques. More particularly, the present disclosure is directed to proton conductive 2DAC films for fuel cell, hydrogen generation and deuterium manufacturing applications.

Background of the Invention

A need exists within the prior art to develop and provide improved performance for fuel cell applications.

SUMMARY

According to first broad aspect, the present invention provides a fuel cell comprising an electrode catalyst assembly and a two-dimensional (2D) amorphous carbon, wherein the 2D amorphous carbon has a crystallinity (C)≤0.8.

According to a second broad aspect, the present invention provides a fuel cell comprising an electrode catalyst assembly and a two-dimensional (2D) amorphous carbon, wherein the 2D amorphous carbon has a crystallinity (C)<1 and a sp3/sp2 bond ratio is 0.2 or less.

According to a third broad aspect, the present invention provides a fuel cell comprising an electrode catalyst assembly and a two-dimensional (2D) amorphous carbon having an atomic structure consisting of non-hexagonal carbon rings and hexagonal carbon rings, and having a ratio of the hexagonal carbon rings to the non-hexagonal carbon rings is less than 1.0.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION OF THE INVENTION

Definitions

Figure 1:
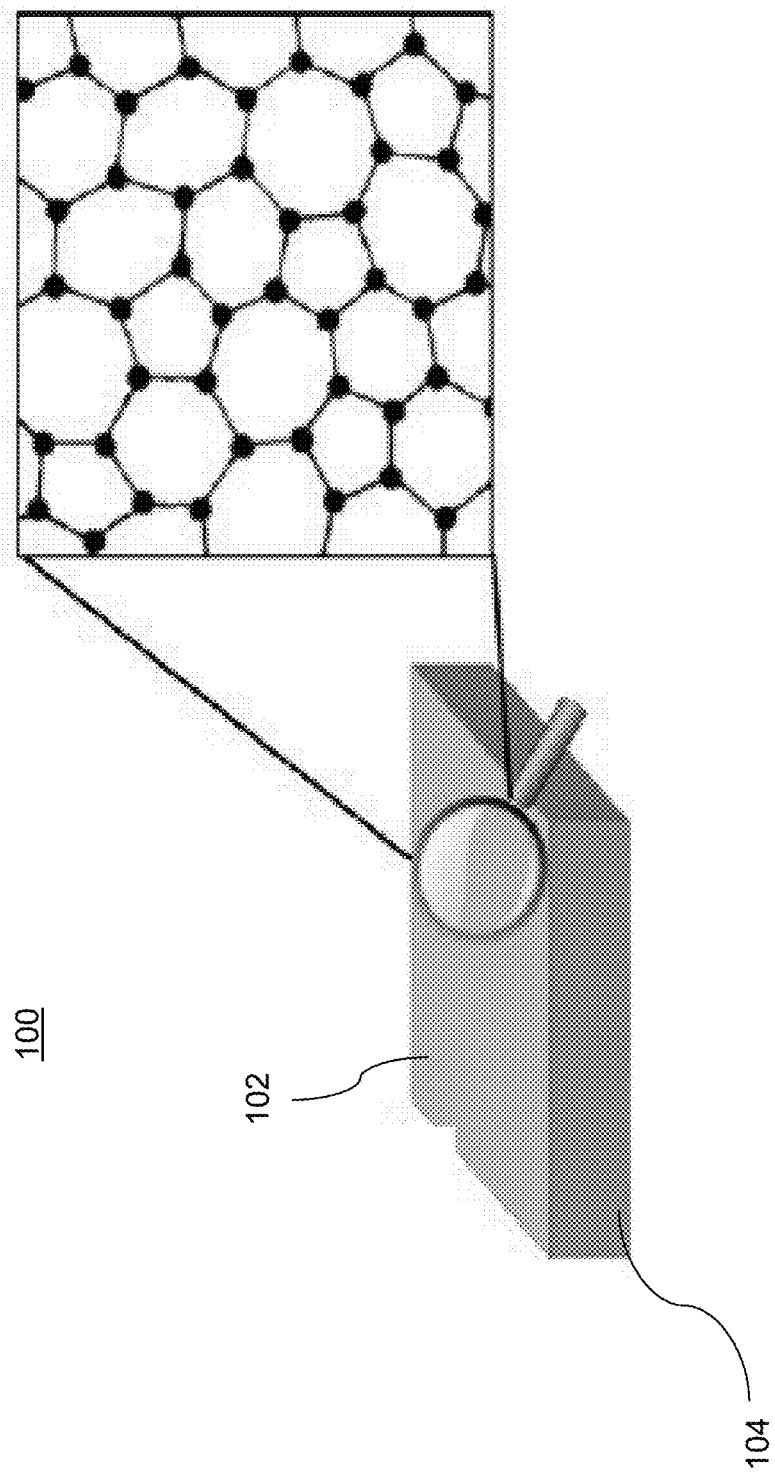
FIG. 1 is a schematic illustration showing the disclosed composite material of the atomically thin film showing random hexagon rings showing continuity and order (not graphene), according to one embodiment of the present disclosure.

Where the definition of terms departs from the commonly used meaning of the term, applicant intends to utilize the definitions provided below, unless specifically indicated.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the"

include plural referents unless the context clearly dictates otherwise. In this application, the use of "or" means "and/or" unless stated otherwise. Furthermore, use of the term "including" as well as other forms, such as "include", "includes," and "included," is not limiting.

For purposes of the present invention, the term "comprising", the term "having", the term "including," and variations of these words are intended to be open-ended and mean that there may be additional elements other than the listed elements.

For purposes of the present invention, directional terms such as "top," "bottom," "upper," "lower," "above," "below," "left," "right," "horizontal," "vertical," "up," "down," etc., are used merely for convenience in describing the various embodiments of the present invention. The embodiments of the present invention may be oriented in various ways. For example, the diagrams, apparatuses, etc., shown in the drawing figures may be flipped over, rotated by 90° in any direction, reversed, etc.

For purposes of the present invention, a value or property is "based" on a particular value, property, the satisfaction of a condition, or other factor, if that value is derived by performing a mathematical calculation or logical decision using that value, property or other factor.

For purposes of the present invention, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

For purposes of the present invention, the term "adhesion strength" refers to the strength of the bonding between the disclosed 2DAC film to its growth substrate. It is directly dependent on the adhesion energy between these two materials, which may be measured in $J/m^2$.

For purposes of the present invention, the term "amorphous" refers to lacking definite form or having no specific shape or being formless. As a non-crystalline solid, amorphous refers to a solid that lacks the long-range order that is characteristic of a crystal.

For purposes of the present invention, the term "amorphous carbon" refers to carbon that does not have any long range crystalline structure.

For purposes of the present invention, the term "atomically thin amorphous carbon" refers to amorphous carbon that consist of approximately one to five layers of carbon atoms in a plane, with predominantly $sp^2$ bonding between the carbon atoms and thus forming a layer. It should be appreciated that layers may be stacked, and this stacking of layers is considered within the scope of the invention.

For purposes of the present invention, the term "carbon coating" refers to a layer of carbon deposited on a substrate.

For purposes of the present invention, the term "carbon ring size" refers to the size of a ring of carbon atoms. In some disclosed embodiments, the number of atoms in one carbon ring may vary from 4 to 9 atoms.

For purposes of the present invention, the term "diamond-like carbon" refers to amorphous carbon that consist of predominantly $sp^3$ bonding between carbon atoms.

For purposes of the present invention, the term "differentiating stem cells" refers to the process of directing an unspecialized stem cell towards a specific type of cell with functional traits. In disclosed embodiments, the differentiation occurs due to a combination of chemical and substrate induced factors.

For purposes of the present invention, the term "DIG ratio" refers to the ratio of the intensities of the D and G peak in the Raman spectrum.

For purposes of the present invention, the term "electrochemical cell (EC)" refers to a device capable of either generating electrical energy from chemical reactions or facilitating it otherwise. The electrochemical cells which generate an electric current are called voltaic cells or galvanic cells and the other ones are called electrolytic cells which are used to drive chemical reactions like electrolysis. A common example of an galvanic cells is a standard 1.5-volt cell meant for consumer use. A battery may consist of one or more cells, connected in either parallel or series pattern.

For purposes of the present invention, the term "fuel cell" refers to an electrochemical cell that converts the chemical energy from a fuel into electricity through an electrochemical reaction of hydrogen fuel with oxygen or another oxidizing agent. Fuel cells may differ from batteries in requiring a continuous source of fuel and oxygen (usually from air) to sustain the chemical reaction, whereas in a battery the chemical energy comes from chemicals already present in the battery. Fuel cells can produce electricity continuously for as long as fuel and oxygen are supplied.

For purposes of the present invention, the term "graphene" refers to an allotrope (form) of carbon consisting of a single layer of carbon atoms arranged in a hexagonal lattice. It is the basic structural element of many other allotropes of carbon, such as graphite, charcoal, carbon nanotubes and fullerenes. It can be considered as an indefinitely large aromatic molecule, the ultimate case of the family of flat polycyclic aromatic hydrocarbons. Graphene has many unusual properties including its strong materials properties, ability to efficiently conduct heat and electricity and is also nearly transparent.

For purposes of the present invention, the term "membrane" refers to layer acting as a selective barrier that may allow some elements to pass through but stopping others such as molecules, ions, or other small particles.

For purposes of the present invention, the term "Nafion®" refers to a sulfonated tetrafluoroethylene based fluoropolymer-copolymer. It is the first of a class of synthetic polymers with ionic properties called ionomers. The unique ionic properties of Nafion® are a result of incorporating perfluorovinyl ether groups terminated with sulfonate groups onto a tetrafluoroethylene (Teflon) backbone. Nafion® serves as a proton conductor for proton exchange membrane (PEM) fuel cells and possesses excellent thermal and mechanical stability.

For purposes of the present invention, the term "proton exchange membrane" or "polymer electrolyte membrane" (PEM), refers to a semipermeable membrane generally made from ionomers and designed to conduct protons while acting as an electronic insulator and reactant barrier, e.g. to oxygen and hydrogen gas. In some embodiments, the proton exchange membrane or polymer electrolyte membrane may also be referred to as a proton conducting membrane. Part of the essential function of the PEM may include separation of reactants and transport of protons while blocking a direct electronic pathway through the membrane. PEMs can be made from either pure polymer membranes or from composite membranes, where other materials are embedded in a polymer matrix. In some disclosed embodiments, PEMs may be primarily characterized by proton conductivity (a), methanol permeability (P), and thermal stability. PEM fuel cells may utilize a solid polymer membrane (a thin plastic film) as the electrolyte wherein the polymer is permeable to protons when it is saturated with water, but it does not conduct electrons.

For purposes of the present invention, the term "proton exchange membrane fuel cell (PEMFC)" refers to a type of fuel cell being developed mainly for transport applications, as well as for stationary fuel-cell applications and portable fuel-cell applications. Their distinguishing features include lower temperature/pressure ranges (50 to 100° C.) and a special proton-conducting polymer electrolyte membrane. PEMFCs generate electricity and operate on the opposite principle to polymer electrolyte membrane (PEM) electrolysis, which consumes electricity. They are a leading candidate to replace the aging alkaline fuel-cell technology. In some applications, PEMFC may also be known as polymer electrolyte membrane fuel cells.

For purposes of the present invention, the term "proton transport" refers to the transport of the proton across an electrically insulating membrane.

For purposes of the present invention, the term "Raman spectroscopy" refers to a spectroscopic technique used to observe vibrational, rotational, and other low-frequency modes in a system. Raman spectroscopy is commonly used in chemistry to provide a structural fingerprint by which molecules can be identified. It relies on inelastic scattering, or Raman scattering, of monochromatic light, usually from a laser in the visible, near infrared, or near ultraviolet range. The laser light interacts with molecular vibrations, phonons or other excitations in the system, resulting in the energy of the laser photons being shifted up or down. The shift in energy gives information about the vibrational modes in the system.

For purposes of the present invention, the term "Raman spectrum" refers to a phenomenon of scattering intensity as a function of frequency shifts depending on rovibronic states of a molecule. For a molecule to exhibit a Raman effect, there must be a change in its electric dipole-electric dipole polarizability with respect to the vibrational coordinate corresponding to the rovibronic state. The intensity of the Raman scattering is proportional to this polarizability change.

For purposes of the present invention, the term "self-assembled" refers to the self-organization of polymer chains in a regular lattice structure covering the disclosed 2DAC surface. In disclosed embodiments, the self-assembly allows for an ultra-thin film formation with different properties compared to bulk properties.

For purposes of the present invention, the term "ratio of $sp^3/sp^2$" refers to the type of carbon bonds found in the 2DAC. The $sp^2$ bonds allow for higher growth factor bonding.

For purposes of the present invention, the term "substrate" refers to the structural support for the disclosed two-dimensional (2D) amorphous carbon film. In select applications, disclosed embodiments provide a substrate to mechanically support, for example, the 2DAC film as, otherwise, the 2DAC film may be too thin to perform its function without getting damaged. The substrate may be regarded as the material used for growth of the disclosed 2DAC or 2DAC film on the surface of the substrate.

For purposes of the present invention, the term "two-dimensional (2D) amorphous carbon film" refers to atomically thin amorphous carbon to the thinnest amorphous carbon possible (e.g., single atom thick) that can be grown directly, for example, on substrates including those having low melting temperature, are non-catalytic, and those substrates also including metal, glass and oxides surfaces. The growth on other substrates is made possible due to the low temperature at which the disclosed 2DAC film is grown. Disclosed embodiments of 2DAC film may be presented as a free-standing film or as a coating on a substrate as disclosed herein. Although the disclosed 2DAC film is amorphous, the carbon atoms bond to multiple adjacent carbon atoms in plane to form a strong network, which is very stable even when it is released from its growth substrate (free-standing). The carbon material also possesses properties for adhering to metal surfaces well, thereby ensuring full coverage across the substrate. The intrinsic thinness and the high strength of the disclosed 2DAC thin film also allow it to withstand bending of the metal substrate without breaking.

For purposes of the present invention, the term "two-dimensional (2D) amorphous carbon coating" refers to a 2DAC film directly grown and/or deposited on a substrate. Disclosed embodiments may also include the case where the 2DAC coating is transferred onto or off the substrate.

DESCRIPTION

While the invention is susceptible to various modifications and alternative forms, specific embodiment thereof has been shown by way of example in the drawings and will be described in detail below. It should be understood, however that it is not intended to limit the invention to the particular forms disclosed, but on the contrary, the invention is to cover all modifications, equivalents, and alternatives falling within the spirit and the scope of the invention.

Figure 11:
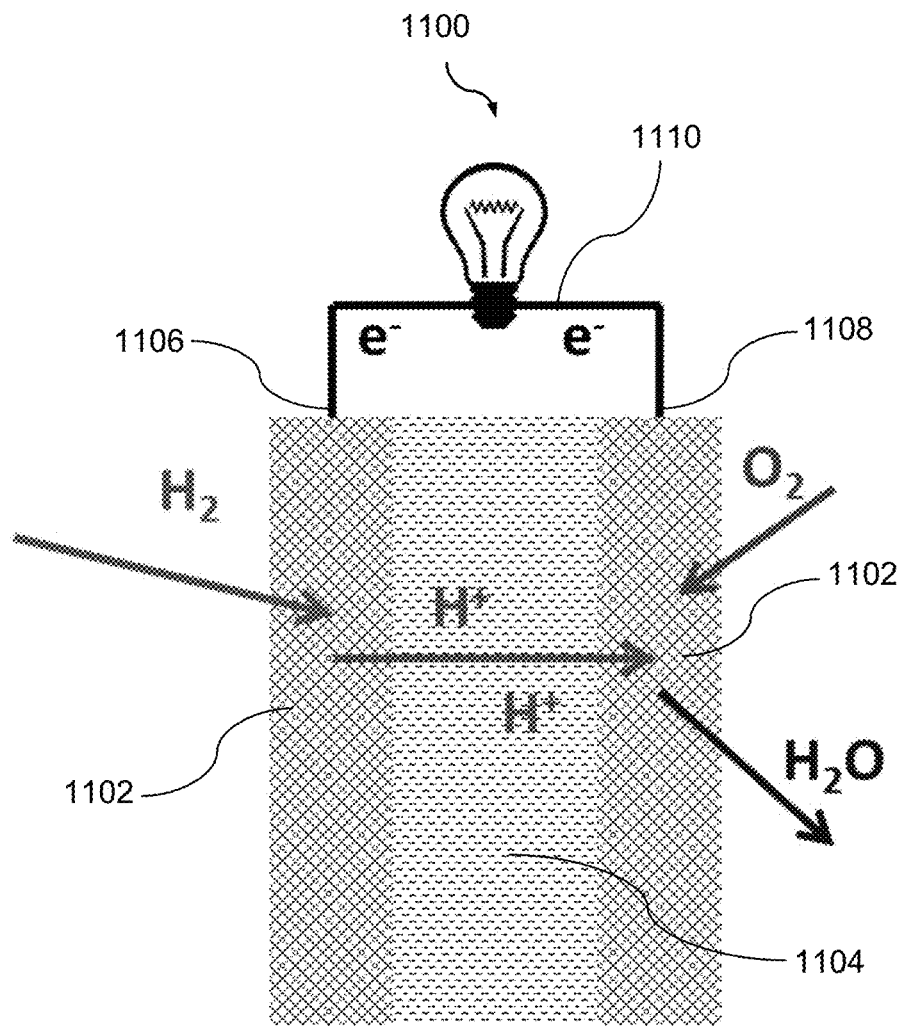
FIG. 11 illustrates a conventional configuration of a proton exchange membrane fuel cell (PEMFC), according to the prior art.

Fuel cells offer a clean and efficient energy conversion of hydrogen and oxygen sources providing electric power and clean water as waste. One of the more promising types of fuel cell is the proton exchange membrane fuel cell (PEMFC), which is already being commercialized.[1] In a conventional configuration, the PEMFC may essentially consists of three components: anode, cathode, and proton exchange membrane. FIG. 11 illustrates the operation principles of an exemplary conventional PEMFC 1100. Hydrogen is disassociated into protons and electrons at the anode 1106 and as the protons cross the proton exchange membrane 1104 to the cathode 108; while the electrons are forced through an external circuit 1110 to reach the cathode 1108. At the cathode 108 the protons interact with the electrons and oxygen, creating water waste ($H_2O$). Power is generated by the electrons in the external circuit 1110.

The performance of PEMFC 1100 is dependent on the proton exchange membrane 1104 to conduct the protons and prevent the hydrogen, methanol, oxygen, nitrogen and other gasses possibly present in the system to cross over the membrane. The electrode/catalyst layer or electrode catalyst assembly 1102 consists of electrodes typically made of carbon decorated with catalyst particles made of platinum, ruthenium or other catalytically active materials. The electrode catalyst assembly 1102 has a porous structure that allows the gasses to diffuse through the layer. The hydrogen fuel diffusing through the anode electrode catalyst assembly reacts with the catalyst particles and is disassociated into protons and electrons. At the cathode electrode catalyst assembly, the oxygen gasses are diffusing through the assembly and is reacting with the protons and electrons to form water. Often an inert gas such as nitrogen is flowed through the system to stabilize the operating pressure, fuel supply, and help carry excess gasses and liquids to the exhaust.

The gas crossing the proton exchange membrane 1104 is of concern, as it not only reduces the net efficiency, but also leads to the formation of hydrogen peroxide at the electrodes, which causes pinholes and thinning of the proton exchange membrane 104. These events reinforce the gas crossover and accelerate the breakdown of the fuel cell.[2]

The gas crossover can also affect the efficiency of the catalyst particles facilitating the chemical reactions at the anode and cathode. The proton exchange membrane 1104 can further be damaged by ionic contaminants such as alkaline metal and ammonium ions.[2]

To prevent the gas crossover and degradation of the proton exchange membrane, embodiments of the disclosed invention provide a 2DAC layer which may be introduced as a gas crossover prevention layer. In some embodiments, the disclosed 2DAC is provided as a film layer. In an exemplary configuration, the disclosed 2DAC film may be attached to proton exchange membrane 1104. The disclosed 2DAC film does not limit the proton conductivity due to its excellent proton conductivity and ultimate thinness. The disclosed 2DAC film is a barrier to all other gasses and ions and thereby increases the lifespan of the employed PEMFC. A further discussion of the disclosed 2DAC film is provided as follows.

Disclosed embodiments relate to a new composite material composed of an atomically thin (single layer) amorphous carbon on top of a substrate (metal, glass, oxides). The amorphous carbon adheres very well to the substrate upon which it is grown. Thus, the amorphous carbon material provides unique characteristics. For example, the disclosed amorphous carbon material is suitable for applications that utilize a substrate requiring a coating for a specific purpose(s). Exemplary applications may include, but not limited to, biomedical applications.

The present disclosure provides a new form of carbon referred to as two-dimensional (2D) amorphous carbon (2DAC). Disclosed embodiments provide the thinnest amorphous carbon possible (e.g., approximately single atom thick) within the 2DAC that can be grown, for instance, directly on metallic substrates including those having low melting temperature, are non-catalytic, and also including glass and oxides surfaces. In one select embodiment, having a single atom thickness is a preferred material and may establish a lower thickness limit for the 2DAC. Disclosed embodiments may include a thickness that may range up to a few atom thickness (e.g., 10 atomic thickness or about 3+ nm). The disclosed 2DAC may be provided as a two-dimensional (2D) amorphous carbon film. It remains important to note, however, that as the thickness of the disclosed 2DAC increases, it remains structurally different (e.g., $sp^3$ to $sp^2$ ratio) from any other possibly existing amorphous carbon material thickness, as disclosed herein.

The growth on other substrates is made possible due to the low temperature at which the disclosed 2DAC film is grown. Although the disclosed 2DAC film is amorphous, the carbon atoms bond to multiple adjacent carbon atoms in plane to form a strong network, which is very stable even when it is released from its growth substrate (free-standing). Thus, each carbon atom is bonded to multiple carbon atoms such that there is a high density of bonds (connections). The disclosed 2DAC also possesses properties for adhering to metal surfaces well, thereby ensuring full coverage. Material properties (e.g., disclosed below), such as the intrinsic thinness and the high strength of the disclosed 2DAC thin film, also allow it to withstand bending of the metal substrate without breaking.

In accordance with disclosed embodiments, amorphous carbon may be defined as a form of carbon with no long-range structural order. It exists in several forms and, depending on its form, is often called in different names like diamond-like carbon, glassy carbon, soot, etc. Amorphous carbon may be produced by several techniques including, for example, chemical vapor deposition, sputter deposition, and cathodic arc deposition among others. In convention applications, amorphous carbon has always existed in three-dimensional form (or in bulk). The two-dimensional equivalent form of carbon is graphene; however, graphene only exists as a crystalline material (either single crystal or polycrystalline). For graphene to be synthesized, it requires high temperatures and is mostly grown on copper. As per this disclosure, disclosed embodiments have managed to create a continuous two-dimensional form of amorphous carbon that is grown at a much lower temperature and on arbitrary substrates. The composite material of the disclosed 2DAC film and substrate has characteristics that are vastly different from the bulk amorphous carbon, and even to single layer graphene.

Embodiments of the disclosed 2DAC may exist as a film, for example, coating a substrate, a film coating an internal surface of a porous structure, a suspended film, a rolled film, a tube, a fiber, or a hollow ball. The mechanical, electrical, optical, thermal and other properties of the disclosed 2DAC are expected to be varying, for example, depending on the shape of the 2DAC. For example a tube comprising the disclosed 2DAC will have high mechanical strength in the axial direction and softer response in the radial direction. One might prepare the disclosed 2DAC into various forms to utilize the different properties for separate applications.

FIG. 1 illustrates a schematic 100 of the disclosed composite materials with a TEM image of the carbon material on a top surface of a substrate. The composition of the disclosed matter is a new composite material of an atomically thin amorphous carbon 102 on top of a substrate 104 (e.g., metal or glass, oxides).

The disclosed composite material may refer to an atomically thin 2D amorphous carbon (2DAC) on top of an arbitrary substrate. In accordance with disclosed embodiments, the disclosed 2DAC film on top of the disclosed substrate may be defined in terms of its atomic structure and its properties.

Figure 2:
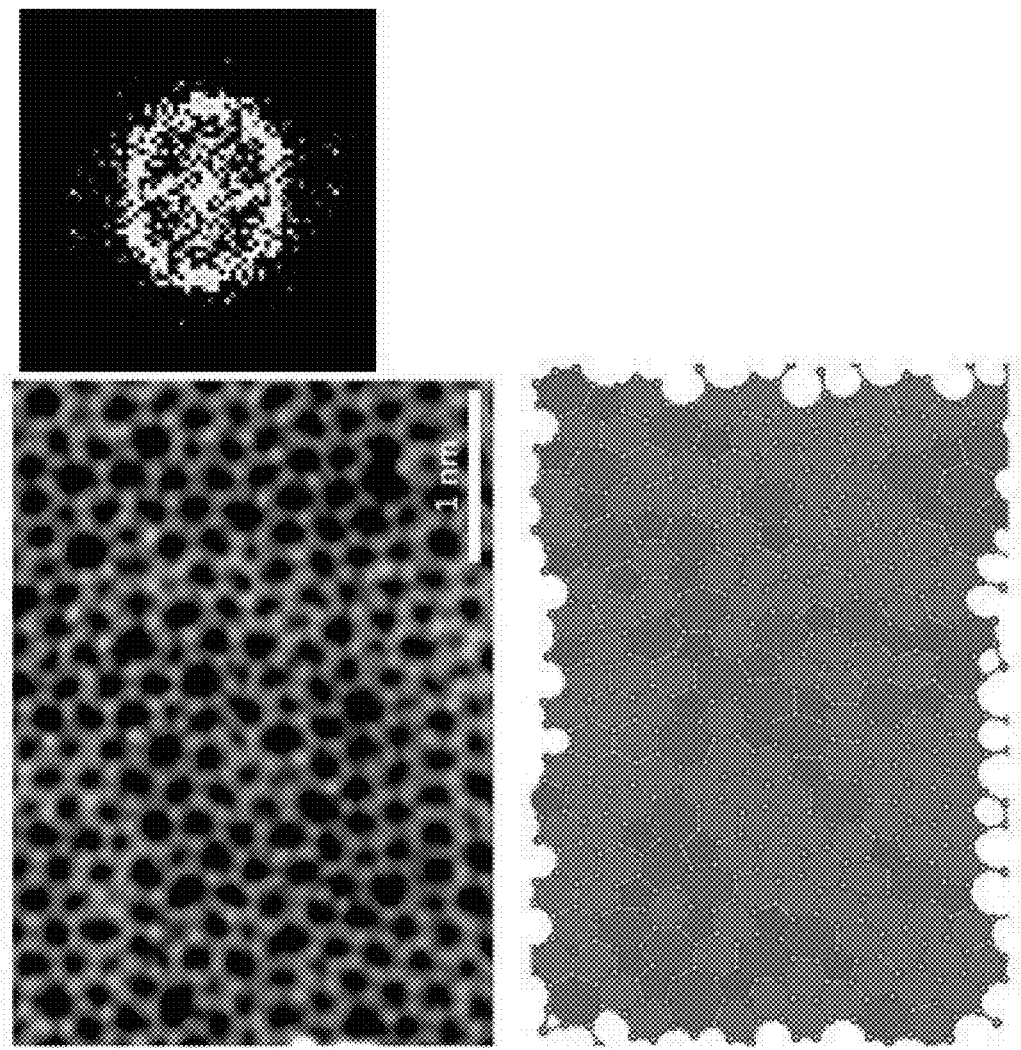
FIG. 2 illustrates a TEM image of an amorphous film showing the hexagons and non-hexagons, according to one embodiment of the present disclosure.

A closer examination and definition for the atomic structure may be presented as follows: FIG. 2 illustrates a TEM image of an amorphous film showing the hexagons and non-hexagons, according to one embodiment of the present disclosure. The upper left image of FIG. 2 illustrates a high resolution TEM image of the disclosed 2DAC film comprising hexagons and non-hexagons. A lower left schematic of the TEM image of the upper left image is provided to aid in viewing. Hexagons are colored in green, while non-hexagons are colored in either red or blue. The upper right display is an FFT illustrating which shows a ring structure with no clear diffraction patterns.

Referring to the TEM image of FIG. 2, a 2DAC film is a single-atom thick carbon film having a mixture of hexagon and non-hexagon rings in its structure. The rings are fully connected to each other, forming a network of polygons in large area film whose scale is at least in microns. The ratio of hexagons to non-hexagons is a measure of crystallinity (or amorphousity), C. Non-hexagons are in a form of 4-, 5-, 7-, 8-, 9-membered rings. A 2D amorphous film has C≤0.8, taken on a minimum imaged area of approximately 8.0 $nm^2$. The C value in FIG. 2 is approximately 0.65. Disclosed embodiments may support a C value range between and including 0.5 to 0.8. This is different from graphene where C=1 for pure hexagonal network. The non-hexagons can be randomly distributed within the hexagonal matrix, or form along the boundaries of the hexagonal domains. The domains must not be greater than 5 nm. The fast Fourier transform (FFT) of the image must not show diffraction spots (FIG. 2, upper right). The 2DAC can be released from a substrate to be free-standing or can be transferred to other substrates. Thus, in some embodiments, the disclosed 2DAC may be separating from the surface of the substrate to obtain a free-standing 2DAC film.

Figure 3:
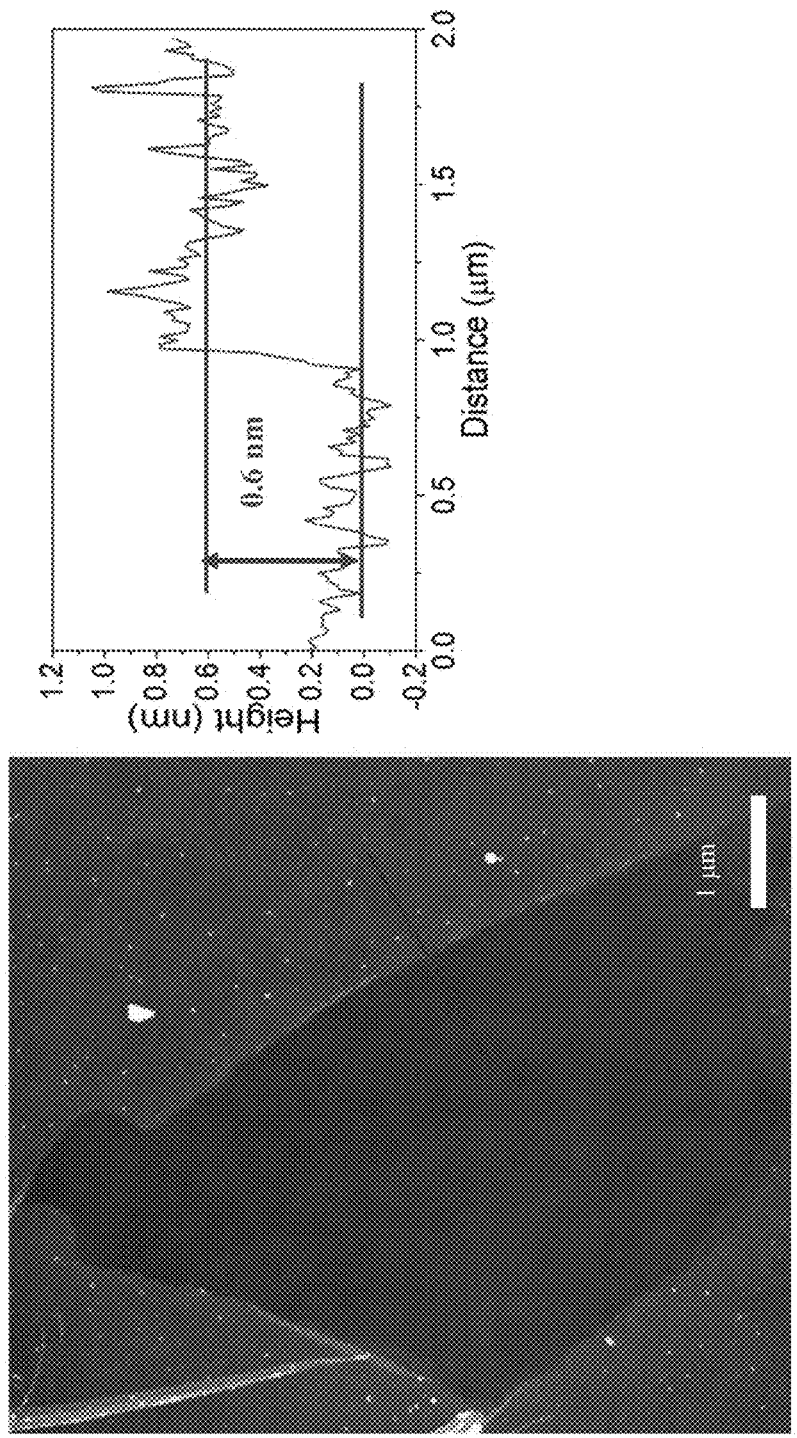
FIG. 3 illustrates a measured thickness of the disclosed carbon film on boron nitride by Atomic Force Microscopy (AFM), according to one embodiment of the present disclosure.

FIG. 3 illustrates a measured thickness (i.e., the height) of the isolated disclosed 2DAC film on boron nitride (BN) by AFM. Based on the disclosed invention, the following properties apply: FIG. 3 shows the AFM of the disclosed transferred 2DAC film to boron nitride (BN). The disclosed thickness of the 2DAC is approximately 6 Å, comparable to graphene which is only one atomic thick (thickness ranges from and including 3.3 Å to 10 Å when measured on BN). The thickness is also corroborated by the TEM image in FIG. 1. Further, the film is found to be homogenous.

Figure 4:
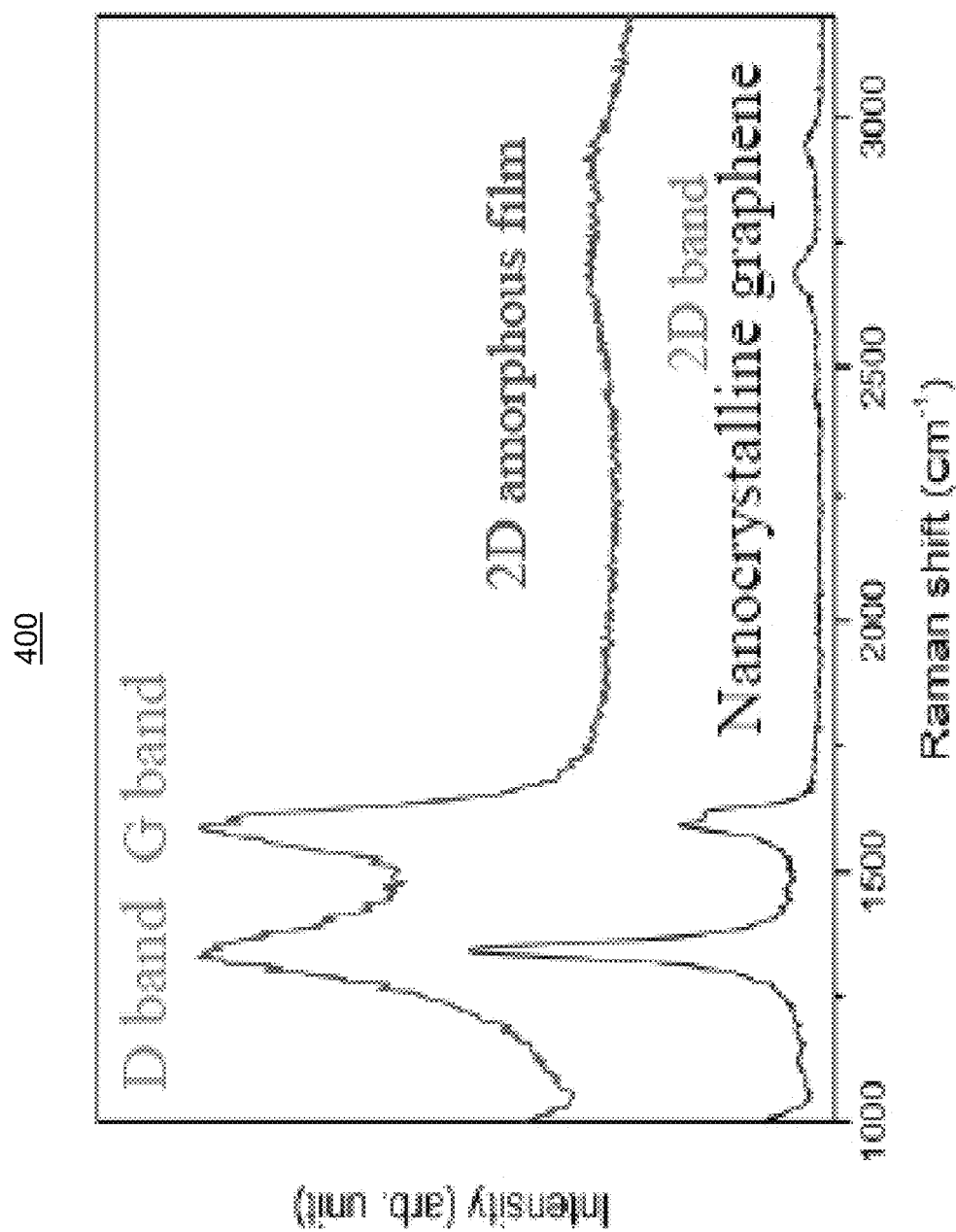
FIG. 4 illustrates a Raman spectra of amorphous film and nano-crystalline graphene on $SiO_2$, according to one embodiment of the present disclosure.

FIG. 4 illustrates Raman spectra 400 of amorphous film and non-crystalline graphene on $SiO_2$. Raman spectroscopy of the isolated film showed no 2D peak (~2700 cm-1), but instead showed broad G (at ~1600 cm-1) and D peaks (at ~1350 cm-1). The broadening of D and G peaks usually indicates a transition from nanocrystalline graphene to amorphous film as was previously reported.[3] From the intensity ratio of the D and G peaks, the domain size is estimated to be in the order of 1-5 nm.[3] Raman spectroscopy serves as a characterization tool to represent the TEM image in FIG. 2 in large area.

Figure 5:
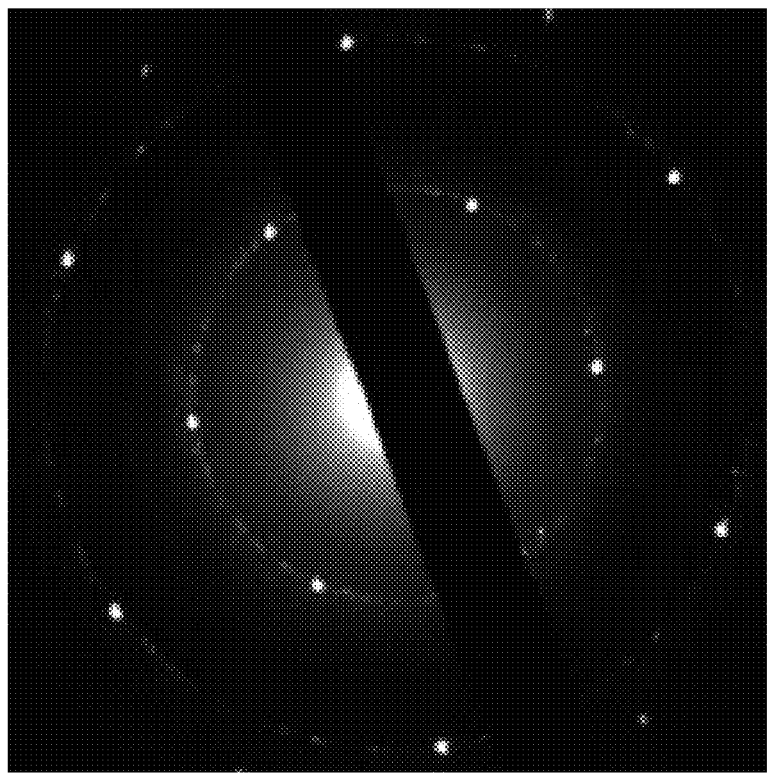
FIG. 5 illustrates TEM diffraction of atomically thin amorphous carbon (left) and graphene (right), according to one embodiment of the present disclosure.
Figure 5:
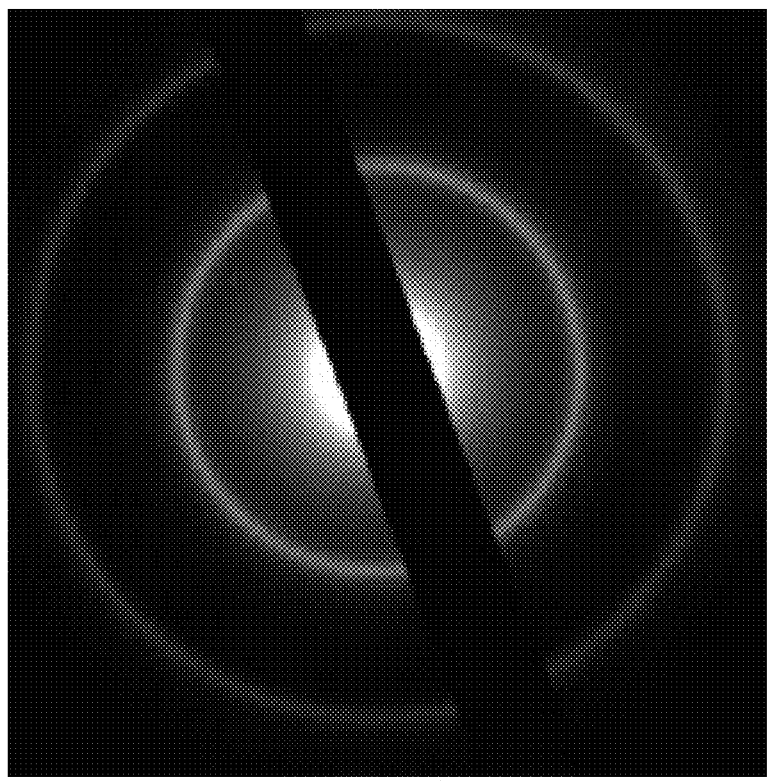

FIG. 5 provides a comparison 500 of TEM diffraction of atomically thin amorphous carbon (left) and graphene (right), according to one embodiment of the present disclosure. Further evidence on the amorphous nature of the disclosed isolated film is corroborated by the TEM diffraction, where no clear diffraction spots are detected which is in contrast to graphene wherein diffraction spots are clearly seen indicating crystallinity. The diffraction rings in FIG. 7 (top) indicates a domain size of <5 nm. The diffraction data of the amorphous film is consistent with the FFT image in FIG. 2. In this case, the 2DAC film is free-standing.

Figure 6:
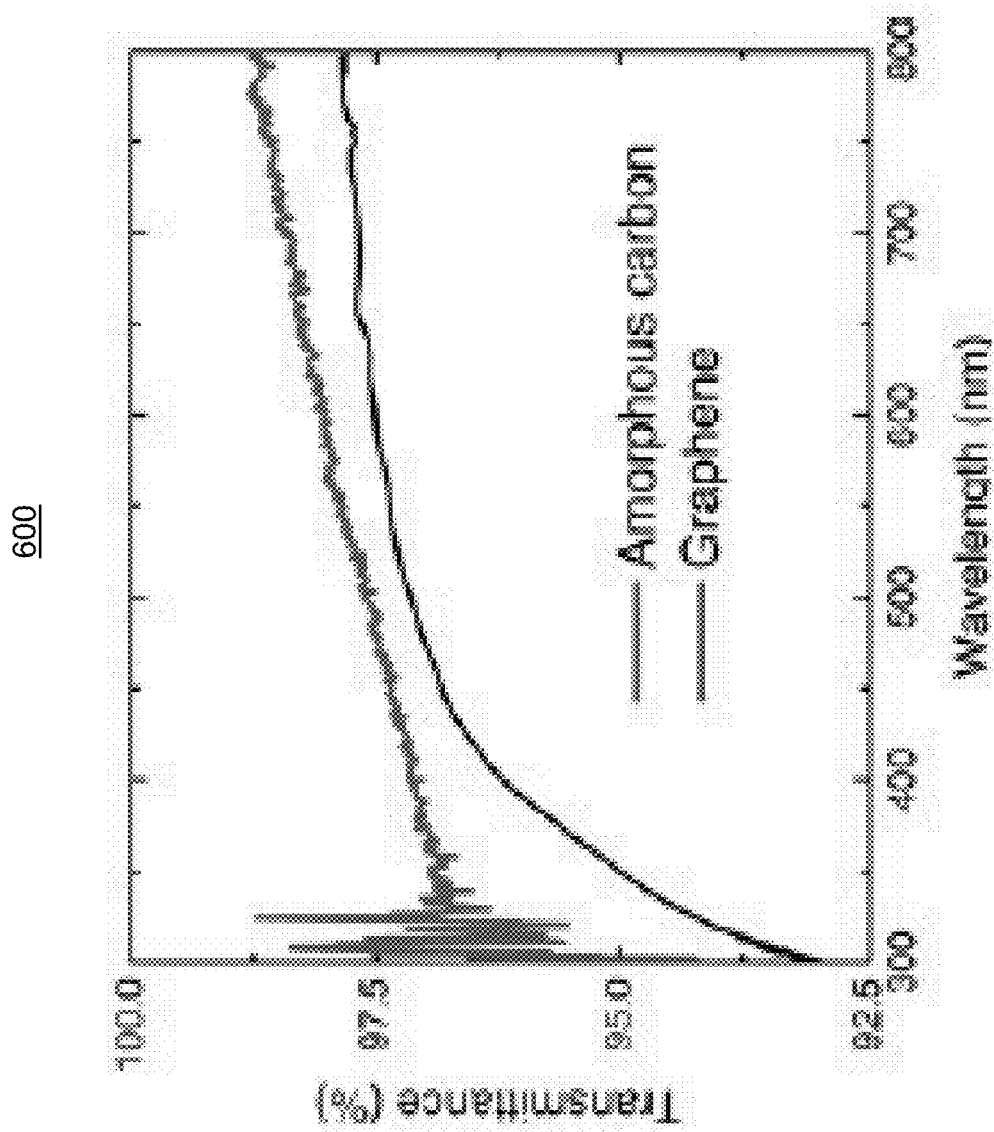
FIG. 6 illustrates the transmittance of the disclosed carbon film, according to one embodiment of the present disclosure.

Turning to FIG. 6, a graph 600 illustrates the transparency of the disclosed carbon film, according to one embodiment of the present disclosure. The optical transparency is at ~98% at 550 nm light wavelength, increasing in transparency with increasing wavelength. Thus, select embodiments provide an optical transparency equal to or greater than 98% at a wavelength of 550 nm or higher. Again, the disclosed carbon film differs from graphene as the transparency of graphene at a single layer is at a maximum of 97.7% throughout the visible wavelength (400 nm-700 nm, inclusive), and decreases as the number of layer increases. Notably the transparency of the 2DAC film does not decrease rapidly at short wavelengths (<400 nm) as seen in graphene.

Figure 7:
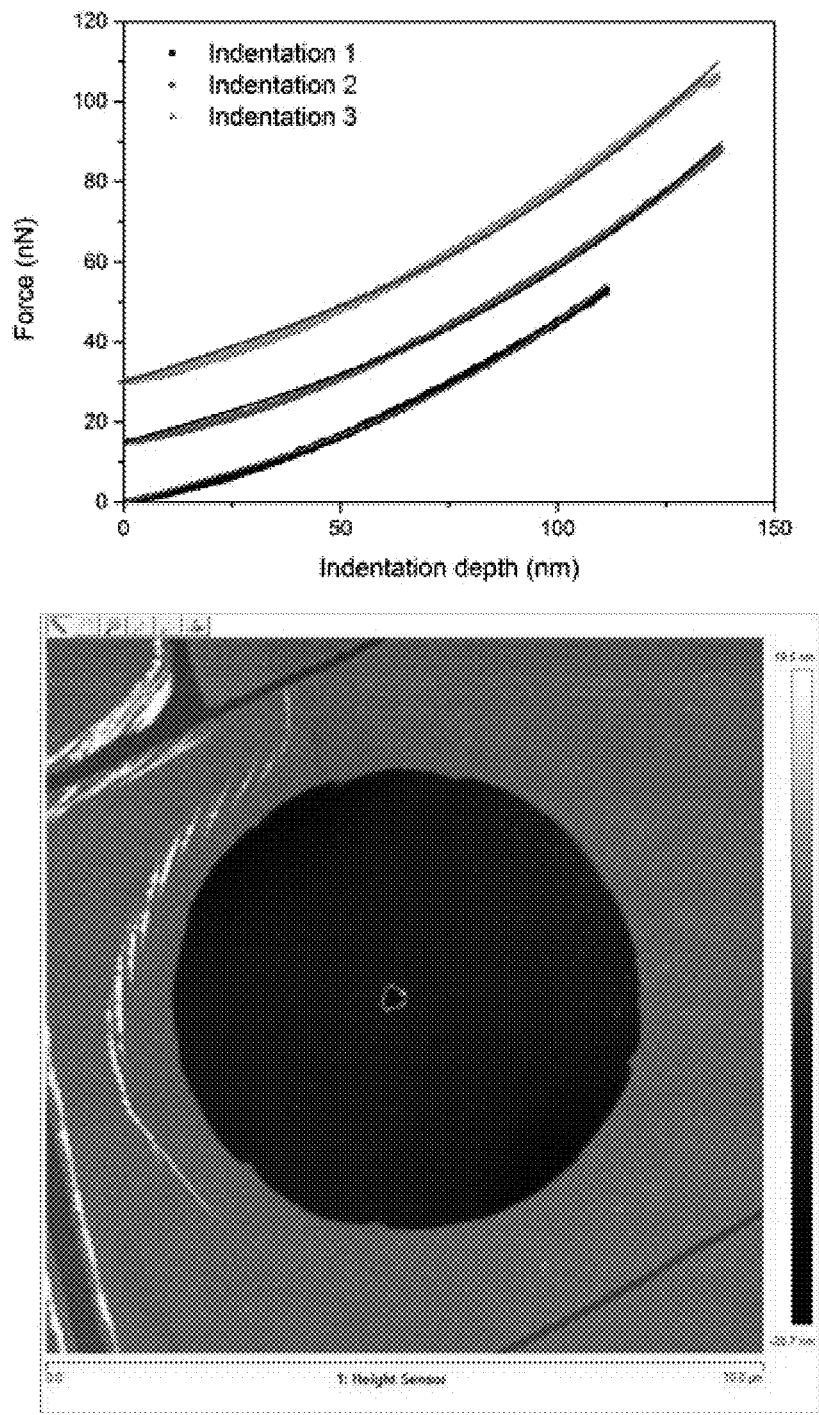
FIG. 7 illustrates a mechanical property of a 2D amorphous film and a demonstration of suspended carbon film, according to one embodiment of the present disclosure.

The elastic modulus, E, of the suspended film is above 200 GPa, higher than bulk glassy carbon (E=60 GPa).[4] The ultimate strain before mechanical failure is 10%, much higher than that of other amorphous carbon reported. FIG. 7 illustrates non-indentation on suspended carbon film and suspended carbon film after exertion of ultimate stress by an Atomic Force Microscope (AFM) (e.g., Bruker model no: MPP-11120) tip. The amorphous property of the disclosed 2DAC film prevents collapse of the suspended film in FIG. 7 (bottom). Instead, the film displays a ductile response to ultimate stress levels.

Figure 8:
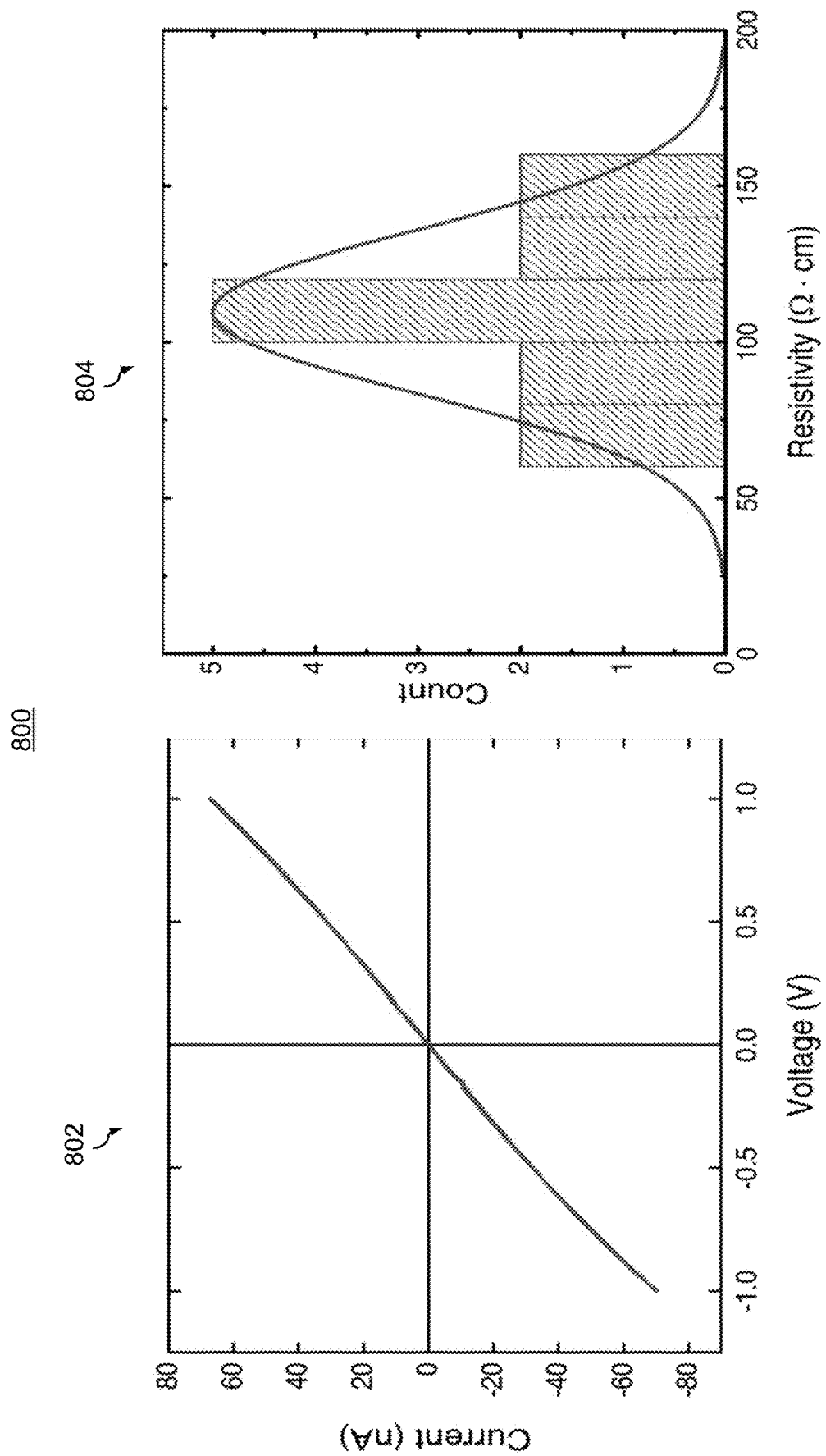
FIG. 8 illustrates electrical properties of a 2DAC, according to one embodiment of the present disclosure.

The 2DAC thin film of the disclosed invention is highly resistive with electrical resistivity ranging from 0.01 to 1000 Ω-cm, depending on the value of C, which is tuned by the growth conditions. FIG. 8 is a schematic illustration 800 of electrical properties of a 2D amorphous carbon, showing an I-V curve 802 of the 2D amorphous film and a histogram 804 of the measured resistivity values for a particular C value. A measurement technique/method is used towards generating a resistivity value. A ratio is used within the calculation from the data of I-V curve 802 to obtain each resistivity data point in histogram 804. Accordingly, length: width ratio for the 2D amorphous carbon in FIG. 8, left is 1:100. In comparison, graphene has resistivity value of $~10^{-6}$ Ω-cm while bulk glassy carbon (also 100% C—C $sp^2$) has values ranging from 0.01 to 0.001 Ω-cm.

The monolayer film, containing n-membered rings>6, is naturally a membrane that can selectively pass gases, ions, liquids or other species whose sizes are small enough to pass through the 7-,8-,9-membered rings. In particular, the disclosed 2DAC film can pass through proton 10× more efficient than crystalline monolayer boron nitride at room temperature.[5] For the disclosed 2DAC film, the resistivity to proton flow across the membrane is from 1-10 Ω-$cm^2$ at room temperature.

Figure 9:
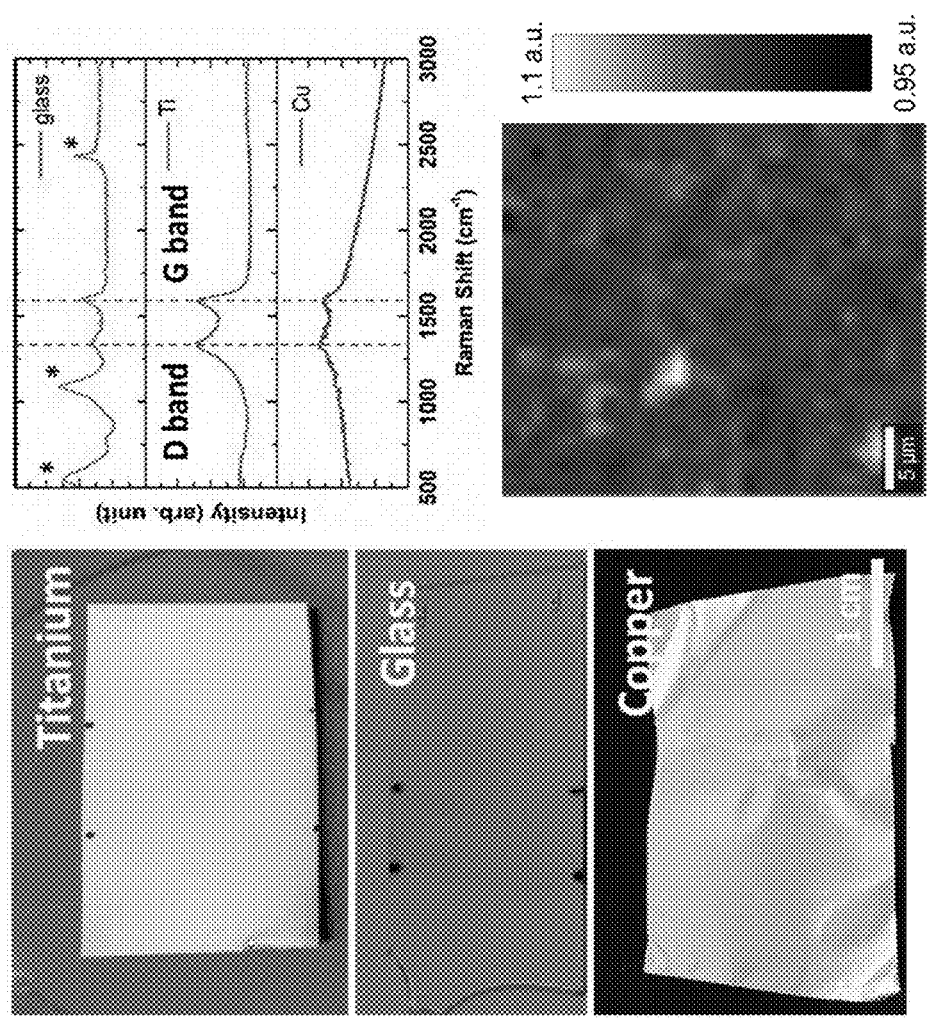
FIG. 9 illustrates composite material grown on different substrates, according to one embodiment of the present disclosure.

FIG. 9 illustrates composite material grown on different substrates, according to one embodiment of the present disclosure. Pictures of titanium, glass and copper coated with atomically thin amorphous carbon are illustrated on the left. In the upper right, shown is the Raman spectra from the coated regions showing similar response irrespectively of the substrate. Finally, in the lower right, shown is the Raman map of G/D peak ratio of the 2DAC film on top of the titanium shown its full coverage. The disclosed composite material (i.e., the disclosed 2DAC and the substrate) can be created from any metal (catalytic or non-catalytic) or on glass or oxides. Thus, disclosed embodiments provide that the 2DAC may be grown directly on any of the disclosed desired substrate materials. This is different from graphene, which can only be grown on a catalytic substrate, e.g., copper, and requires transfer to all other substrates. Accordingly, compared to deposition methods of amorphous or diamond-like carbon, whose thickness cannot exist lower than 1 nm to still be considered continuous, the disclosed composite material comprises an atomically thin (<1 nm) and continuous layer of two-dimensional amorphous carbon that is strongly bonded to a host substrate.

In general, when a film on a substrate has poor adhesion, areas of the film may become detached from the substrate and, therefore, will provide poor or little protection of the substrate. Accordingly, embodiments of the present disclosure provide an improved film which provides uniformity and strong adhesion over the entire applied surface of a substrate. Accordingly, the disclosed 2DAC film is formed as a continuous film over, preferably, substantially the entire substrate surface or at least the applied surface. Unlike conventional designs, such as graphene, for example, in Cu, which can be detached easily (e.g., the adhesion force is from 10-100 J/m2), the disclosed atomically thin 2DAC film disposed, for example, on Cu adheres very well to the substrate with an adhesion energy>200 J/m2.[6] This example provides further evidence to differentiate the disclosed 2DAC film from graphene. (While an exemplary embodiment of a Cu substrate is described, embodiments of applying the disclosed 2DAC to any substrate may be applied in accordance with disclosed embodiments of the invention.) Furthermore, the adhesion energy is evident in all substrate materials onto which the disclosed 2DAC film is grown including, for examples, stainless steel, titanium, glass, nickel, and aluminum substrates. It should be appreciated that the above substrates are exemplary and the teachings of this disclosure may be applied to any substrate desired.

In general, any attempts for transferring any 2D material to a material by convention materials and processes have previously led to defects and cracks, for example, in the transferred material(s) and also a reduction of coverage on the substrate. This is, at least in part, due to the fact that the transfer process generally employs many mechanical steps and may use chemicals that induce cracks and defects in conventional film applications. The disclosed 2DAC film, however, does not need to be transferred, for example, from a growth substrate to a target substrate. In addition to the improved adhesion properties of the disclosed 2DAC film, enhanced characteristics of the disclosed 2DAC film provide and ensure consistent and full coverage directly across/over the substrate. Consistent and full coverage is thereby obtained, at least, because, there is no need to transfer the disclosed 2DAC film, since it is fully capable of consistently and successfully being grown directly on its host substrate.

Designed to provide such dependable coverage, together, along with its superior mechanical properties for adhesion to substrates (such as carbon), the disclosed 2DAC film is very suitable and dependable for applications that require additional physical characteristics/requirements of the 2DAC film and composite. Such physical characteristics may include the ability of the disclosed 2DAC film and/or composite to bend and/or stretch. The adhesion properties and ability of the disclosed 2DAC to the substrate ensures this is the case. If there is non-uniform adhesion to the substrate, like for transferred films, cracks in the film will form at regions of poor adhesion and are causes prone to failure.

Accordingly, embodiments of the disclosed invention provide the top amorphous carbon film 102 covering the whole substrate 104 upon which it is grown (Raman map of FIG. 9) making it very useful for applications that require, for example, carbon coating. The top amorphous carbon film 102 also serves as a diffusion barrier without defects thereby preventing the underlying substrate from oxidation and corrosion. Due to electrically insulating properties, the disclosed amorphous carbon film 102 prevents any galvanic corrosion of substrate 104. The low electrical conductivity of the disclosed 2DAC is beneficial to cell attachment and proliferation as observed in recent reports.[7] Cells on conductive substrates adhere to the surface through electrostatic interactions without creating focal adhesions. Focal adhesions are crucial to cell proliferation and growth and a low electrical conductivity is preferred for focal adhesion development and cell proliferation. The low electrical conductivity is a consequence of the amorphous nature of the disclosed 2DAC as observed through the Raman spectroscopy D/G peak intensity and the $sp^3/sp^2$ ratio.

In contrast, graphene is known to worsen long term corrosion.[8] The transfer of graphene makes it nearly impossible to create a flat continuous film without creating cracks and defects along the surface. The disclosed amorphous carbon film 102 material is a composite with substrate 104, hereby eliminating the need for transfer as well as removing the risk of cracks in the film 102.

Figure 10:
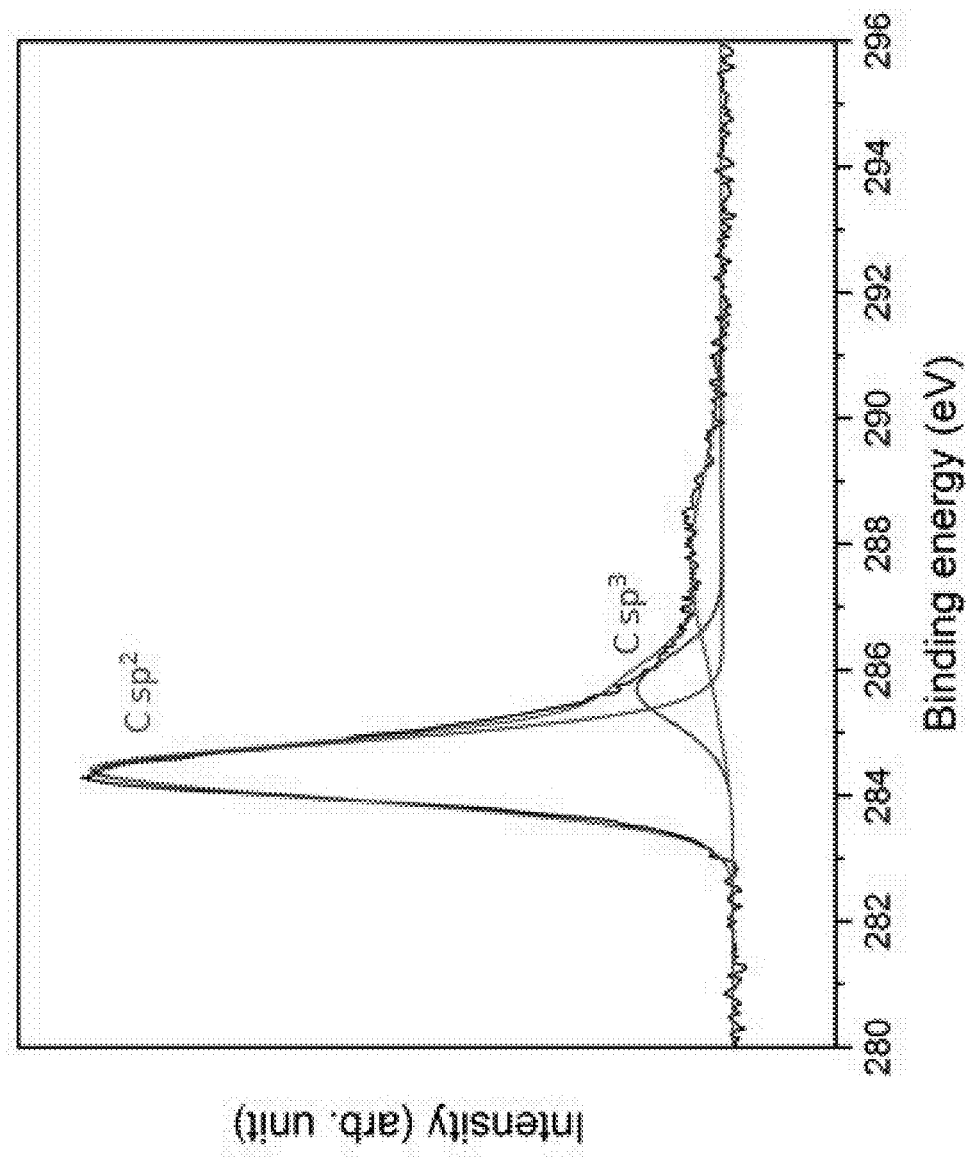
FIG. 10 illustrates X-ray photoelectron spectroscopy (XPS) of a 2DAC on Cu, according to one embodiment of the present disclosure.

The disclosed 2DAC film consists of $sp^2$-bonded carbon similar to glassy carbon; however the thickness is only approximately one atomic layer thick (6 Å), thinner than any conventional reported amorphous carbon structure. FIG. 10 illustrates the X-ray photoelectron spectroscopy (XPS) measurement of 2D amorphous carbon on Cu, where the peak position indicates the $sp^2$ or $sp^3$ bonding type while the peak intensity indicates the fraction of each type of bonds. A mix concentration of C—C $sp^2$ and $sp^3$ bonding is also possible without sacrificing the thickness, though the maximum C—C $sp^3$ content is set to 20%. The thin structure and strong adhesion of the disclosed 2DAC intrinsically protects the underlying substrate all the time, unlike in thicker films where the possibility of flaking off is evident.[9]

According to disclosed embodiments, a laser-based growth process, using hydrocarbons as precursors (such as $CH_4$, $C_2H_2$, etc.) produces the disclosed composite film. Hydrogen gas ($H_2$) and Argon gas (Ar) may also be mixed with the precursor. In this process, the laser has two roles: (1) an energy source to breakdown the precursor gas in a process called photolytic decomposition; and (2) as a local heat source. Assuming that one or both aforementioned roles produces the disclosed 2DAC film: in the first case, the substrate 104 is said to be at room temperature throughout the growth; in the second case, the laser can heat up the substrate 104 up to 500° C. Typically, a pulsed excimer UV laser (e.g., 193, 248 or 308 nm) can be directed onto or parallel to the substrate at a fluence from about 50-1000 $mJ/cm^2$ at different growth times, depending on the employed substrate. Other possible combinations to produce the disclosed composite may include utilizing any combination of a laser, plasma, and/or a substrate heater. A heater may be employed to heat the substrate 104 up to 500° C. Plasma power may be used in the range of and including 1-100 W. A typical combination using hydrocarbon as precursor will be as follows: (i) Laser only; (ii) Laser+low power plasma (5 W); (iii) Laser+low power plasma (5 W)+heater (300° C.-500° C.); (iv) Low power plasma (5 W)+500° C. heater; (v) High power plasma (100 W) only.

According to disclosed embodiments, the entire growth/deposition of the disclosed 2DAC and 2DAC composite may be performed within a chamber. Modules for heating, plasma, gas flow and pressure control may all be set and established within the chamber for the controlled growth environment. According to one embodiment, the process pressure of the chamber may be established in a range of, and including, 10 to 1 E-4 mbar.

The process parameters for the disclosed 2DAC may include the following: (i) process gas: $CH_4$ (ii) chamber pressure: 2.0 E-2 mbar; (iii) laser fluence: 70 $mJ/cm^2$; (iv) growth time: 1 min; (v) plasma power: 5 W; (vi) substrate: Cu foil.

A process for producing the disclosed 2DAC film may employ the use of methane ($CH_4$) within the growth chamber for the growth process. The gas pressure within the chamber during the growth is controlled at 2 E-2 mbar throughout. This gas is in the presence of a plasma generator operating at 5 W power. The growth starts when the 248 nm excimer laser is exposed on the surface of the copper foil substrate with a fluence of 70 $mJ/cm^2$ with a pulse frequency of 50 Hz. The laser exposure time (i.e., growth duration) is set at 1 min to obtain a continuous 2DAC coating on the substrate. In this growth, the stage heater is not used. Multiple parameters disclosed herein may be adjusted, for controlling and/or changing the properties of the disclosed 2DAC including, but not limited to, hydrocarbons as precursors, precursor mixes, adjustments to the photolytic decomposition process and equipment, temperature regulations, substrate temperature adjustment, the change in C value, change in number of atomic layers, change in $sp^2$ to $sp^3$ ratio, and change in adhesion to substrate.

The disclosed carbon film may be constructed with minimal thickness thereby ensuring that the disclosed metal surface of the substrate is consistently and completely covered during the lifetime of applied usage. In one exemplary embodiment, the disclosed 2DAC thickness may be designed at approximately one atomic layer thick. The disclosed carbon film 102 may be grown directly on several substrates 104, for example, such as stainless steel and titanium materials. Since the growth is done at much lower temperature than, for example, graphene synthesis, the disclosed 2DAC may be grown directly to other substrates 104 that cannot withstand high temperature like glasses and hard discs.[10] The disclosed 2DAC film 102 is ultra-strong and is strongly bounded to the substrate 104 making it suitable for applications that may require deformation such as bending and stretching. The strong mechanical properties of the disclosed 2DAC film is due to its lack of grain boundaries. The insulating property of the disclosed carbon film 102 prevents galvanic corrosion of the substrate 104 unlike graphene which enhances the corrosion. The 7-,8-, and 9-membered rings of the carbon film, as seen in the TEM image, is useful as an efficient membrane for gases or for proton transport.[5]

According to select embodiments of the disclosed invention, the disclosed 2DAC may be generated as a free-standing case, for example, when a substrate is not suitable to be grown on, and hence the disclosed 2DAC needs to be transferred. Suitable methods and techniques for transferring the disclosed 2DAC 1202 may be employed such as dry transfer as described in the patent application: Defect-free direct dry delamination of cvd graphene using a polarized ferroelectric polymer WO2016126208A1. Other transfer methods may include, but not limited to, thermal release tape, pressure-sensitive adhesive, spin coating, spray coating, and Langmuir-Blodgett technique.

However, additional advantages of the present disclosure provide that, in some embodiments, the disclosed 2DAC 1202 may be directly grown on a substrate. Such benefits of the disclosed 2DAC film compared, for example, to graphene for the transfer process is that the disclosed 2DAC film does not require a sacrificial support layer for transfer (unlike graphene). With graphene, the film layer is required to prevent cracks and defects during the transfer, and the film layer needs to be removed after. Even with removal, there residues remain from the sacrificial layer that cannot be completely removed. With the disclosed 2DAC, the transfer can be done without the sacrificial layer, without inducing defects and without dealing with residues or compromising the structure.

Advantages of the disclosed embodiments of the 2DAC layer may be implemented in a wide variety of applications including, but not limited to: fuel cell, hydrogen generation and deuterium manufacturing applications. Such applications make use of the advantages of the disclosed 2DAC layer including, for example, an exemplary single layer of carbon atoms in a non-crystalline structure having a C-value below or equal to 0.8. Referring, again, to the amorphous nature of the disclosed 2DAC layer, such as the 2DAC film shown in FIG. 2, the continuous film of carbon is arranged in a random patterned that allows for an ultra-high transverse conductance of protons between approximately 0.1-10 $S/cm^2$. The conductance of deuteron (nuclei of deuterium) is 0.01-1 $S/cm^2$, roughly an order of magnitude lower than that of protons. The conductance of trition (nuclei of tritium) is approximately 0.003-0.3 $S/cm^2$. The difference in transport rates makes the disclosed 2DAC an efficient separation membrane for hydrogen isotopes. At the same time the membrane is impermeable to other molecules such as $H_2$, $O_2$ and $CH_4$.

The proton transport through the film is limited by the electron cloud density.[5] The C-value describes the crystallinity of the disclosed 2DAC and can be controlled/adjusted between approximately 0.5 to 0.8 by changing the growth parameters. By modifying the C-value, the electron cloud in the film is modified and can increase or decrease the proton conductance. For example, applied techniques may include adjusting the power, pulse and/or angle of an employed laser to the disclosed 2DAC.

In select embodiments, the elastic modulus, E, of the disclosed 2DAC suspended film is above 200 GPa and the fracture energy is >20 J/m2, more than twice that of graphene. Evidence of the same is illustrated, for example, in FIG. 3 wherein a nano-indentation on the disclosed suspended 2DAC film showing elastic modulus E>200 GPa (right) suspended 2DAC film after exertion of ultimate stress by an AFM tip indicating a fracture energy>20 $J/m^2$. Thus, the characteristics of these mechanical properties of the disclosed 2DAC layer increases the lifetime of the applications. For example, the disclosed barrier prevents gas cross over and, thereby, prevents corrosion of the electrolyte and catalyst layer. The strong mechanical properties of the disclosed 2DAC layer and specifically high fracture toughness of the same ensures long lifetime of the employed barrier, thereby generating a longer overall performance of the fuel cell.

The disclosed 2DAC layer or film can be further modified during growth or post-processing by other non-limited techniques including, for example: reactive oxygen ion plasma, argon sputtering, ozone treatment, or electron beam exposure. The atomic structure of the disclosed 2DAC may be modified to allow larger molecules to pass through. This is utilized to create a gas separator.

Example Subject Matter

Example 1

Figure 12:
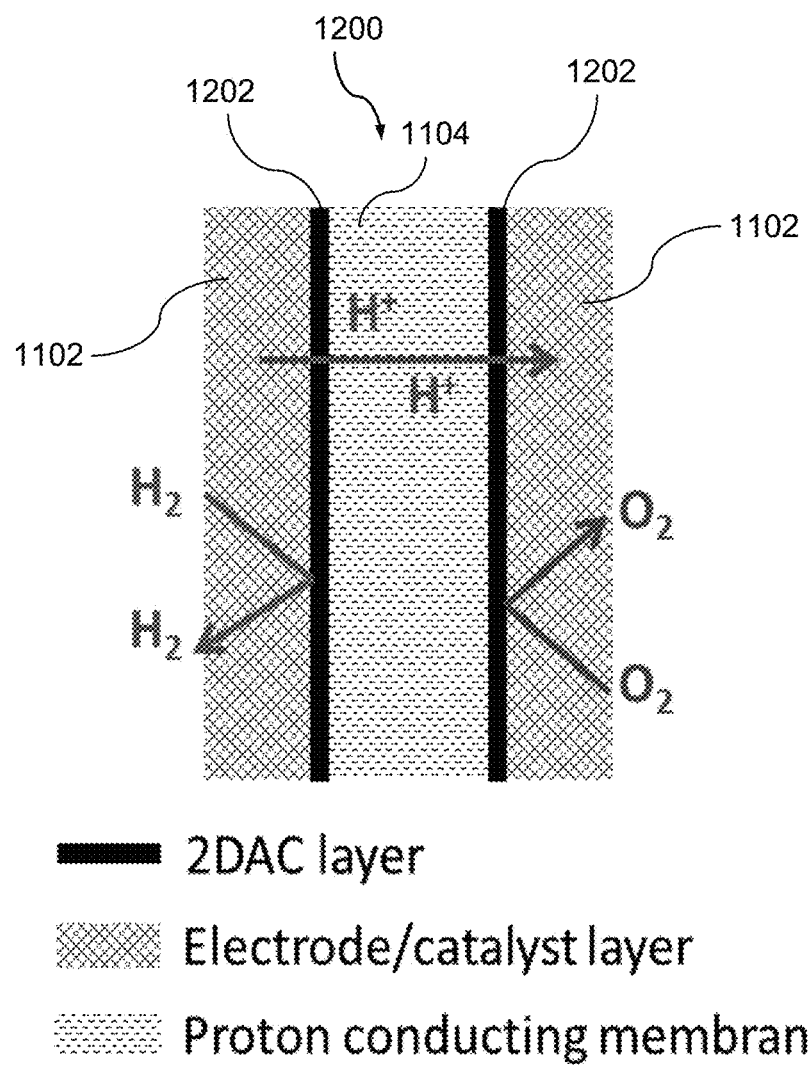
FIG. 12 illustrates an embodiment implementing 2DAC as a barrier layer between electrodes and a proton exchange membrane, according to one embodiment of the present disclosure.

2DAC in Fuel Cell as Anti-Gas Crossover Layer:

FIG. 12 illustrates an exemplary embodiment of an improved PEMFC 1200, according to one disclosed embodiment, wherein the disclosed 2DAC serves as a proton conducting barrier layer. PEMFC 1200 includes the disclosed 2DAC 1202 employed as a barrier layer between electrode catalyst assembly 1102 and proton exchange membrane 1104. The disclosed 2DAC 1202 allows only protons to cross the 2DAC layer 1202 and prevents other gases and liquids from contact with the proton exchange membrane 1104.

In this exemplary configuration, multiple electrode catalyst assembly 1102 are disposed to encapsulate the disclosed 2DAC 1202 and proton exchange membrane 1104. The disclosed 2DAC 1202 may be disposed between each electrode catalyst assembly 1102 and proton exchange membrane 1104. Acting as a barrier, 2DAC 1202 prevents fuel, waste, and ion contaminants from leaking into proton exchange membrane 1104 and crossing to the opposite electrode catalyst assembly 1102. Such leaks are known to cause breakdown of proton exchange membrane 1104 and degradation of the PEMFC performance. It is readily appreciated that the disclosed 2DAC may be employed as is or other configuration such as a layer, membrane, film, etc.

The hydrogen and oxygen crossing proton conducting membrane 1104 can be directly accounted as loss of fuel and a direct loss to the fuel cell efficiency. The disclosed 2DAC 1202 will prevent this loss and may significantly improve the efficiency of the fuel cell. Without 2DAC 1202, other gasses, such as nitrogen, can otherwise also pass through the proton conducting membrane 1104. This, in turn, may lead to fuel starvation, for example, at the catalyst sites. Such starvation is known to lead to catalyst degradation and, hence, loss of performance and reliability.[11] The disclosed 2DAC 1202 will prevent other gasses from crossing the proton conducting membrane 1104 and prevent the aforementioned catalyst degradation.

Proton exchange membranes 1104 often require a high level of hydration to conduct protons. By encapsulating the proton conducting membrane 1104 in a non-permeable barrier, dehydration and dying of the proton conducting membrane 1104 can be prevented. This will lead to long term stability of the PEMFC 1200 performance.

Those skilled in the art will readily appreciate that the disclosed technique is not limited to PEMFC applications, but may also be implemented in other applications such as redox flow batteries.

Example 2

Figure 13:
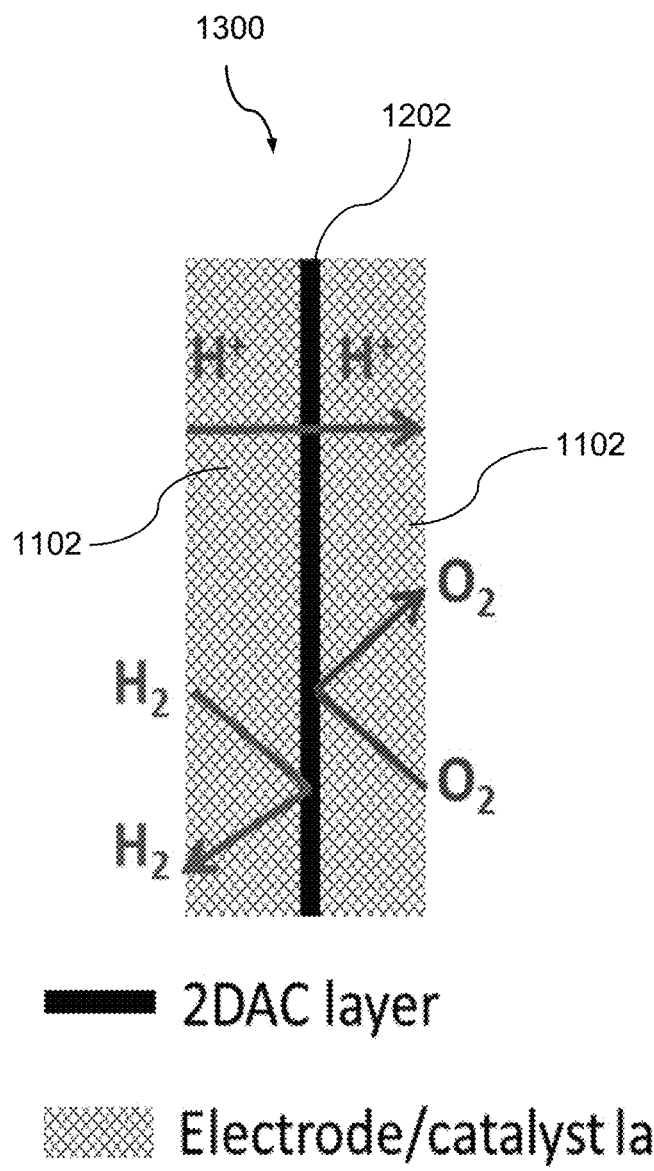
FIG. 13 illustrates an embodiment implementing 2DAC in a configuration between anode and cathode assemblies, according to one embodiment of the present disclosure.

2DAC as a Single Atomic Layer Proton Exchange Membrane:

FIG. 13 illustrates an exemplary embodiment of an improved PEMFC 1300, according to a disclosed embodiment, wherein the disclosed 2DAC is employed as a single atomic proton conducting membrane. This embodiment disposes the disclosed 2DAC 1202 in a configuration between the anode and cathode assemblies. In this configuration the proton exchange membrane has been replaced by a single atomic layer of 2DAC 1202.

The single atomic layer of the disclosed 2DAC 1202 conducts protons and prevents fuel gasses and liquids from crossing there through. This reduces the need for hydration of a traditional proton exchange membrane. The high proton conductivity across the ultrathin 2DAC 1202 generates high power with less ohmic losses than otherwise achieved and observed in traditional proton exchange membranes. The 2DAC layer 1202 is mechanically strong and possesses high fracture toughness providing long term stability. The flexibility of the 2DAC 1202 allows for novel creations of the thin flexible fuel cells.

Example 3

Figure 14:
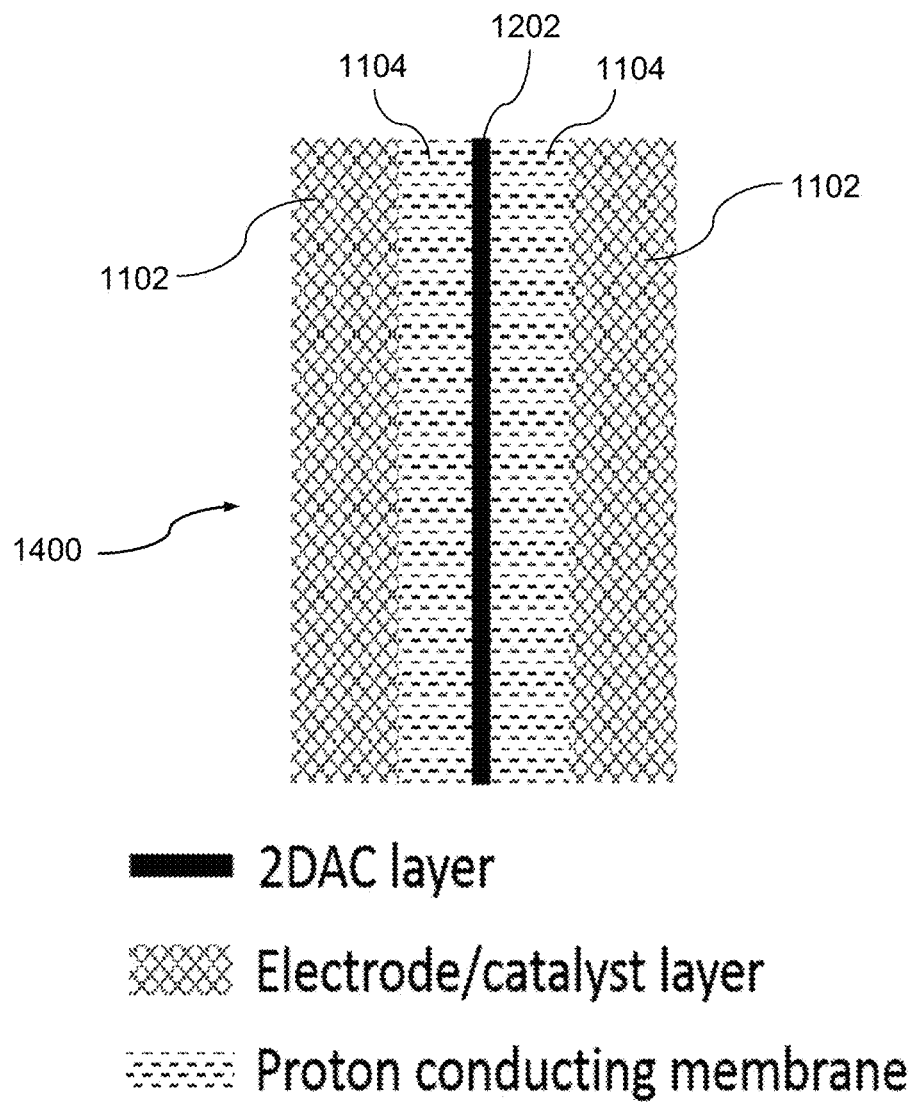
FIG. 14 illustrates an embodiment wherein Nafion® is formed on either side of an exemplary 2DAC film and encapsulated between electrode and catalyst layers in a fuel cell configuration, according to one embodiment of the present disclosure.

Self-Assembled Ultrathin Uniform Proton Exchange Membranes on 2DAC:

FIG. 14 illustrates an exemplary embodiment of an improved PEMFC 1400, according to a disclosed embodiment, wherein the proton conducting membrane 1104 is employed as a self-assembled Nafion® proton conducting membrane or coating 1104 formed on the disclosed 2DAC 1202. Hence, the proton exchange membrane 1104 may be comprised of a fluoropolymer such as Nation®. Proton exchange membrane 1104 is usually formed with a minimum thickness of approximately tens of microns to avoid gas crossover, and a maximum thickness of approximately a few hundred microns to reduce transport losses across proton exchange membrane 1104.

The disclosed 2DAC 1202 may serve as a template for polymer assembly due to its unoccupied pi-orbitals. The amorphous structure of the disclosed 2DAC 1202 acts as a template for the Nafion® polymer to form a thin film. Even though the disclosed 2DAC has low crystallinity, the pi orbitals in the carbon rings allow for alignment of the Nafion® polymer to the surface. Thus, 2DAC 1202 may be utilized to create ultrathin uniform layers of Nafion® coatings 1104 on the 2DAC surface. The aforementioned Nafion® coatings 1104 do not have pinholes. The proton conductivity of the ultrathin Nafion® coating 1104 is increased, while the leakage and gas crossover is reduced due to the self-assembly on the disclosed 2DAC 1202.

Thus, as shown in the illustrative embodiment of FIG. 14, electrode catalyst assembly 1102 may comprise multiple electrode catalyst assemblies. Proton exchange membrane 1104 may comprise multiple proton exchange membranes. The disclosed 2DAC 1202 may be disposed between multiple proton exchange membranes 1104, and multiple proton exchange membranes 1104 may be disposed between the multiple electrode catalyst assemblies 1102.

Acting as proton exchange membrane 1104, FIG. 14 illustrates that the Nafion® coating can be formed on either side of the 2DAC layer 1202 or film and configured to be encapsulated between electrode catalyst assembly 1102 in a fuel cell configuration. Thus, the disclosed 2DAC 1202 can be transferred, for example, to a Nafion® film by wet transfer similar to that of CVD graphene.[12]

In another exemplary embodiment, the disclosed 2DAC 1202 can also be transferred to a Nafion® membrane by dry transfer as described in the patent application: Defect-free direct dry delamination of cvd graphene using a polarized ferroelectric polymer WO2016126208A1. As noted above, other transfer methods may include but not limited to thermal release tape, pressure-sensitive adhesive, spin coating, spray coating, and Langmuir-Blodgett technique.

Example 4

Figure 15:
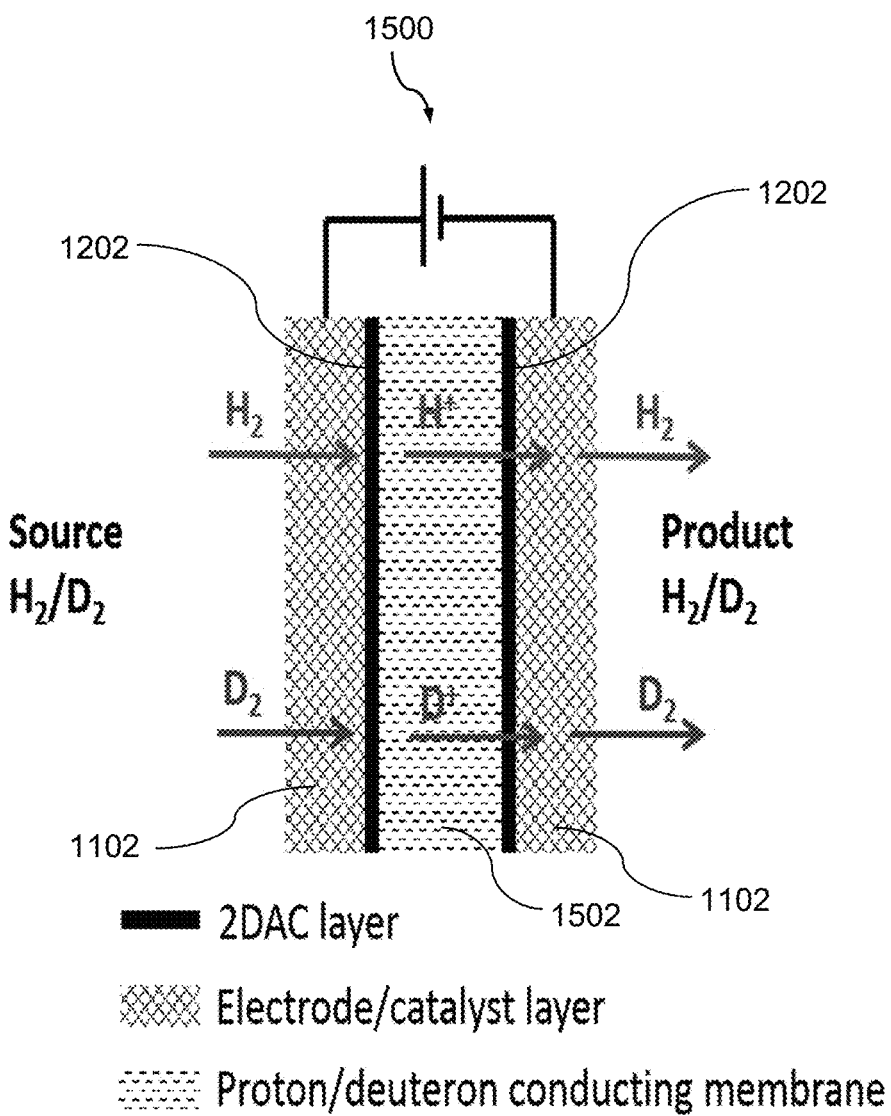
FIG. 15 illustrates an exemplary fuel cell embodiment with 2DAC layers in between the electrode/catalyst assembly and proton/deuteron conducting membranes, according to one embodiment of the present disclosure.

Hydrogen Isotopes Separation:

FIG. 15 illustrates an exemplary embodiment of an improved PEMFC, according to a disclosed embodiment, in which fuel cell 1500 is configured to operate in reverse thereby separating hydrogen isotopes. The disclosed 2DAC 1202 facilitates the transport of the nuclei of hydrogen isotopes deuterium and tritium, although at a much lower rate than proton transport. The difference in transport rates across 2DAC 1202 is used for separation of hydrogen isotopes from protium (standard hydrogen). Such separation can be used for heavy water production, e.g., for use in research and nuclear reactors, as well as removal of tritium, for example, from the heavy water used in nuclear reactors in order to maintain performance.

FIG. 15 illustrates a fuel cell 1500 with 2DAC 1202 in between the electrode catalyst assembly 1102 assembly and proton/deuteron conducting membrane 1502. The fuel cell 1500 is operated in reverse mode by applying a bias across proton/deuteron conducting membrane 1502. In this mode, the fuel cell 1500 consumes electricity and produces hydrogen and deuterium. The hydrogen and deuterium are disassociated into protons and deuterons and are transported across the disclosed 2DAC layers 1202 and proton/deuteron conducting membrane 1502.

As disclosed above, the atomic structure and carbon ring size of the disclosed 2DAC 1202 can be modified (such as through exposure to plasma, e-beam or other irradiation techniques). Thus, the structure of the disclosed 2DAC 1202 may be tuning by modifying the ring size to, thereby, affect different rates of transport of protons and deuterons across disclosed 2DAC layers 1202. The result, of which, may comprise a higher content of hydrogen compared to deuterium.

Thus, in one embodiment, a source ratio of $H_2/D_2$:50% may generate a product ratio of $H_2/D_2$:90%. However, in some disclosed embodiments the source ratio and product ration of $H_2/D_2$ may be varied. For example, if the transport rate for H+ is 10× that of D+, source ratio of $H_2/D_2=1$ and product ratio of $H_2/D_2=10$.

Example 5

Figure 16:
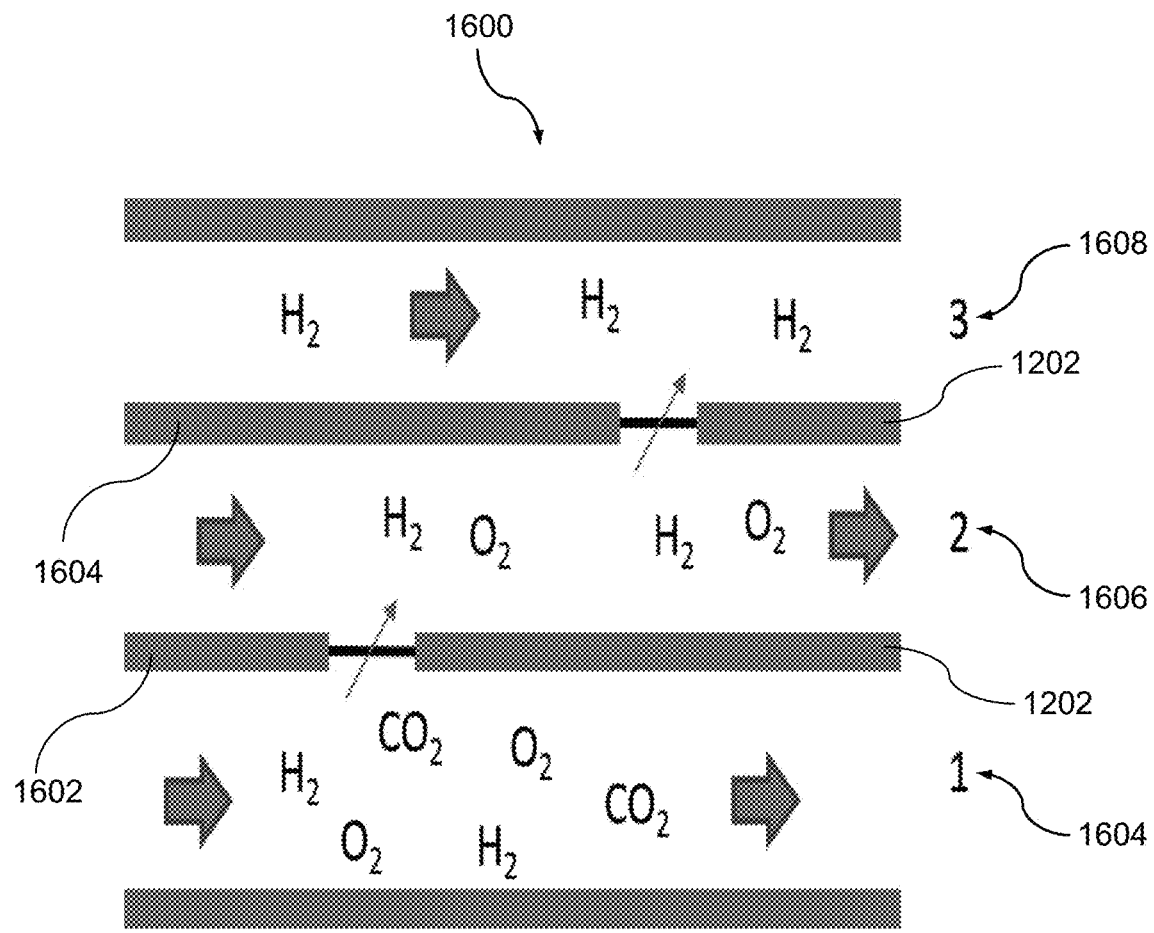
FIG. 16 is an illustrative example of how modified membranes could be used to separate gas mixtures, according to one embodiment of the present disclosure.

Gas Selective Membrane:

FIG. 16 illustrates an exemplary system 1600 for gas separation by the disclosed modified 2DAC 1202, according to a disclosed embodiment. The disclosed 2DAC 1202 can be modified by irradiation techniques, such as electron beam and ionic plasma, to allow larger molecules to pass through, thereby enabling a gas selective membrane. Thus, the disclosed 2DAC 1202 remains a barrier to all molecules larger than specified by the modification parameters.

FIG. 16 illustrates an example of how the disclosed modified 2DAC 1202 may be employed as a membrane or layer utilized, for example, to separate gas mixtures. For example, the modified 2DAC membrane 1602 between stage 1 1604 and stage 2 1606 may be modified to allow $H_2$ and $O_2$ to pass through; and modified 2DAC membrane 1604 between stage 2 1606 and stage 3 1608 may be modified to allow only $H_2$ to pass through. By applying a negative pressure gradient from stage 1 to stage 3, and recycling the gasses through the system 1600, stage 1 will only contain $CO_2$, stage 2 will only contain $O_2$, and stage 3 will only contain $H_2$. Thus, gas separation is achieved in system 1600.

In summary, the two-dimensional amorphous carbon (2DAC), of the disclosed embodiment, may comprise a single atomic layer of carbon atoms in a non-crystalline amorphous structure. In its original state, the random arrangement of atoms allows for high transverse proton conductivity, and barrier for all larger atoms and molecules (e.g., $H_2$, $O_2$, $CH_4$). This highly proton conductive membrane can be implemented, for example, in fuel cell, hydrogen generation and deuterium manufacturing applications.

The atomic structure and carbon ring size of the disclosed 2DAC can be modified through exposure to plasma, e-beam or other irradiation techniques. This allows for larger molecules to pass through thereby expanding the use of the disclosed 2DAC into numerous gas separation applications. The disclosed 2DAC is unique in that it possesses extremely high proton conductivity while introducing only a single atomic layer of thickness. The mechanical toughness, as compared, for example, to other two-dimensional materials, means that the disclosed 2DAC requires approximately three times more energy for a crack to propagate in the disclosed 2DAC. The disclosed 2DAC is impermeable to molecular hydrogen and larger molecules. Thus, the disclosed 2DAC prevents gas from crossing the proton exchange membrane and, hence, poisoning the electrode catalyst assembly 1102. The disclosed 2DAC possesses a proton transport rate of approximately 0.1-10 $S/cm^2$. Such a high transport rate increases performance over conventional fuel cells. The disclosed 2DAC provides selective transport of hydrogen nuclei isotopes. Thus, the difference in transport rates makes the disclosed 2DAC a more efficient separation membrane for hydrogen isotopes.

Having described the many embodiments of the present disclosure in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

REFERENCES

The following references are referred to above and are incorporated herein by reference:

1. Sharaf, O. Z. & Orhan, M. F. "An overview of fuel cell technology: Fundamentals and applications." *Renewable and Sustainable Energy Reviews* 32, 810-853 (2014).
2. Schmittinger, W. & Vahidi, A. "A review of the main parameters influencing long-term performance and durability of PEM fuel cells." *Journal of Power Sources* 180, 1-14 (2008).
3. Ferrari, A. C. et al. "Interpretation of Raman spectra of disordered and amorphous carbon." *Physical Review B* 61, 14095-14107 (2000).
4. Robertson, J. "Ultrathin carbon coatings for magnetic storage technology." *Thin Solid Films* 383, 81-88 (2001).
5. Hu, S. et al. "Proton transport through one-atom-thick crystals." *Nature* 516, 227-230 (2014).
6. Das, S. et al. "Measurements of adhesion energy of graphene to metallic substrates." *Carbon* 59, 121-129 (2013).
7. Choi, W. J. et al. "Effects of substrate conductivity on cell morphogenesis and proliferation using tailored, atomic layer deposition-grown ZnO thin films." *Scientific Reports* 5, 9974 (2015).
8. Schriver, M. et al. "Graphene as a Long-Term Metal Oxidation Barrier: Worse Than Nothing" *ACS Nano* 7, 5763-5768 (2013).
9. Wang, J. S. et al. "The mechanical performance of DLC films on steel substrates." *Thin Solid Films* 325, 163-174 (1998).
10. Marcon, et. al. "The head-disk interface roadmap to an areal density of 4 Tbit/$in^2$." *Advances in Tribology* 2013, 1-8 (2013).
11. Reiser, C. A. "A reverse-current decay mechanism for fuel cells." *J Electrochem Solid-State Letters* 8, A273-A276 (2005).
12. Li, X. S. et al. Large-Area Synthesis of High-Quality and Uniform Graphene Films on Copper Foils *Science* 324, 1312-1314 (2009).

All documents, patents, journal articles and other materials cited in the present application are incorporated herein by reference.

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A fuel cell comprising:
an electrode catalyst assembly;
a two-dimensional (2D) amorphous carbon, wherein the 2D amorphous carbon has a crystallinity (C)≤0.8, and
a proton exchange membrane,
wherein the 2D amorphous carbon is disposed between the electrode catalyst assembly and the proton exchange membrane.

2. The fuel cell of claim 1, wherein the 2D amorphous carbon is a membrane.

3. The fuel cell of claim 1, wherein the 2D amorphous carbon is a film.

4. The fuel cell of claim 1, wherein the 2D amorphous carbon has a resistivity of 0.01 to 1000 Ω-cm, inclusive.

5. The fuel cell of claim 1,
wherein the electrode catalyst assembly comprises multiple electrode catalyst assemblies,
wherein the proton exchange membrane is disposed between the multiple electrode catalyst assemblies and the 2D amorphous carbon is disposed between each electrode catalyst assembly and the proton exchange membrane.

6. The fuel cell of claim 1,
wherein the electrode catalyst assembly comprises multiple electrode catalyst assemblies,
wherein the proton exchange membrane comprises multiple proton exchange membranes,
wherein the 2D amorphous carbon is disposed between the multiple proton exchange membranes, and the multiple proton exchange membranes are disposed between the multiple electrode catalyst assemblies.

7. The fuel cell of claim 1, wherein the proton exchange membrane is a fluoropolymer.

8. The fuel cell of claim 7, wherein the fluoropolymer is Nafion®.

9. The fuel cell of claim 1, wherein the 2D amorphous carbon has a $sp^3/sp^2$ bond ratio is 0.2 or less.

10. A fuel cell comprising:
an electrode catalyst assembly; and
a two-dimensional (2D) amorphous carbon having an atomic structure consisting of non-hexagonal carbon rings and hexagonal carbon rings,
wherein a ratio of the hexagonal carbon rings to the non-hexagonal carbon rings is less than 1.0,
wherein the 2D amorphous carbon has a crystallinity (C)<1 and a $sp^3/sp^2$ bond ratio is 0.2 or less.

11. The fuel cell of claim 10, wherein the 2D amorphous carbon is a membrane.

12. The fuel cell of claim 10, wherein the 2D amorphous carbon is a film.

13. The fuel cell of claim 10, wherein the 2D amorphous carbon has a resistivity of 0.01 to 1000 Ω-cm, inclusive.

14. The fuel cell of claim 10, further comprising:
a proton exchange membrane.

15. The fuel cell of claim 14, wherein the 2D amorphous carbon is disposed between the electrode catalyst assembly and the proton exchange membrane.

16. The fuel cell of claim 14,
wherein the electrode catalyst assembly comprises multiple electrode catalyst assemblies,
wherein the proton exchange membrane is disposed between the multiple electrode catalyst assemblies and the 2D amorphous carbon is disposed between each electrode catalyst assembly and the proton exchange membrane.

17. The fuel cell of claim 14,
wherein the electrode catalyst assembly comprises multiple electrode catalyst assemblies,
wherein the proton exchange membrane comprises multiple proton exchange membranes,
wherein the 2D amorphous carbon is disposed between the multiple proton exchange membranes, and the multiple proton exchange membranes are disposed between the multiple electrode catalyst assemblies.

18. The fuel cell of claim 14, wherein the proton exchange membrane is a fluoropolymer.

19. The fuel cell of claim 18, wherein the fluoropolymer is Nafion®.

* * * * *